United States Patent
Baisch et al.

(10) Patent No.: US 11,311,883 B2
(45) Date of Patent: Apr. 26, 2022

(54) SYSTEMS AND METHODS RELATING TO PORTABLE MICROFLUIDIC DEVICES FOR PROCESSING BIOMOLECULES

(71) Applicants: CONSERVATION X LABS, INC., Northwest, WA (US); UNIVERSITY OF WASHINGTON, Seattle, WA (US)

(72) Inventors: David Baisch, Lynnwood, WA (US); Hallie Ray Holmes, Blacksburg, VA (US); Karl F. Bohringer, Seattle, WA (US)

(73) Assignees: CONSERVATION X LABS, INC., Northwest, WA (US); NATIONAL SCIENCE FOUNDATION, Alexandria, VA (US)

( * ) Notice: Subject to any disclaimer, the term of this patent is extended or adjusted under 35 U.S.C. 154(b) by 181 days.

(21) Appl. No.: 16/758,445

(22) PCT Filed: Oct. 23, 2018

(86) PCT No.: PCT/US2018/056961
§ 371 (c)(1),
(2) Date: Apr. 23, 2020

(87) PCT Pub. No.: WO2019/089268
PCT Pub. Date: May 9, 2019

(65) Prior Publication Data
US 2020/0254459 A1    Aug. 13, 2020

Related U.S. Application Data

(60) Provisional application No. 62/575,523, filed on Oct. 23, 2017.

(51) Int. Cl.
*B01L 3/00* (2006.01)
*B01L 7/00* (2006.01)
*C12Q 1/6844* (2018.01)

(52) U.S. Cl.
CPC ......... *B01L 3/502792* (2013.01); *B01L 7/525* (2013.01); *C12Q 1/6844* (2013.01);
(Continued)

(58) Field of Classification Search
CPC ..... B01L 2200/0621; B01L 2200/0673; B01L 2200/10; B01L 2200/16; B01L 2300/0816;
(Continued)

(56) References Cited

U.S. PATENT DOCUMENTS

2004/0087033 A1    5/2004 Schembri
2008/0053205 A1    3/2008 Pollack et al.
(Continued)

FOREIGN PATENT DOCUMENTS

WO    WO-2017041023 A1  *  3/2017  ............ B01L 3/5027

OTHER PUBLICATIONS

Dong et al., "Converting Vertical Vibration of Anisotropic Ratchet Conveyors into Horizontal Droplet Motion", 'Langmuir', published on Sep. 20, 2017, pp. 2.
(Continued)

*Primary Examiner* — Jennifer Wecker
*Assistant Examiner* — Jonathan Bortoli
(74) *Attorney, Agent, or Firm* — EcoTech Law Group, P.C.

(57) ABSTRACT

Aniosotropic Ratchet Conveyor ("ARC")-based biomolecule processing devices and related methods are described. The ARC-based biomolecule processing devices include (i) a substrate having an ARC track defined on or within the substrate and including a biomolecule receiving area, which is designed to receive biomolecule, and a reconstituting area, which is designed to contain dry reagents and is designed to receive a transport solution such that at the reconstituting area, dry reagents are reconstituted with transport solution;
(Continued)

and (ii) a microheater area disposed at or near the biomolecule receiving area, fitted with a microheater, which is designed to heat biomolecule that is received through the biomolecule receiving area and designed to process heated biomolecule and dry reagents reconstituted with transport solution. The ARC track includes an arrangement of a plurality of hydrophilic rungs disposed on a hydrophobic region such that between consecutive hydrophobic rungs, a portion of the hydrophobic region is exposed.

31 Claims, 16 Drawing Sheets

(52) U.S. Cl.
CPC ............... *B01L 2200/0621* (2013.01); *B01L 2200/0673* (2013.01); *B01L 2200/10* (2013.01); *B01L 2200/16* (2013.01); *B01L 2300/0816* (2013.01); *B01L 2300/0851* (2013.01); *B01L 2300/0867* (2013.01); *B01L 2300/1827* (2013.01); *B01L 2400/0433* (2013.01); *B01L 2400/0688* (2013.01); *B01L 2400/088* (2013.01)

(58) Field of Classification Search
CPC ..... B01L 2300/0851; B01L 2300/0867; B01L 2300/1827; B01L 2400/0433; B01L 2400/0688; B01L 2400/088; B01L 3/502792; B01L 7/525; C12Q 1/6844; C12Q 2531/101; C12Q 2563/159; C12Q 2565/607; C12Q 2565/629
See application file for complete search history.

(56) References Cited

U.S. PATENT DOCUMENTS

| 2008/0124716 | A1  | 5/2008 | Cooney et al. |
| 2012/0115189 | A1  | 5/2012 | Jovanovich et al. |
| 2014/0144518 | A1* | 5/2014 | Bohringer ............... F15D 1/00 137/13 |

OTHER PUBLICATIONS

International Search Report and Written Opinion of International Application No. PCT/US2018/056961 dated Mar. 22, 2019, pp. 22.

* cited by examiner

```
                    ┌──────────┐
                    │  Start   │
                    └────┬─────┘
                         │
                         ▼
    ┌────────────────────────────────────────────┐
    │ Receiving a biomolecule at or near a       │──── 802
    │ biomolecule receiving area                 │
    └────────────────────┬───────────────────────┘
                         ▼
    ┌────────────────────────────────────────────┐
    │ Receiving a transport solution at or near a│──── 804
    │ transport solution receiving area          │
    └────────────────────┬───────────────────────┘
                         ▼
    ┌────────────────────────────────────────────┐
    │ Heating the biomolecule at the heating     │──── 806
    │ area to produce an intermediate biomolecule│
    └────────────────────┬───────────────────────┘
                         ▼
    ┌────────────────────────────────────────────┐
    │ Reconstituting dry reagents into transport │
    │ solution at the reconstituting area to     │──── 808
    │ produce a reconstituted reagent solution   │
    └────────────────────┬───────────────────────┘
                         ▼
    ┌────────────────────────────────────────────┐
    │ Conveying, using a vibration-driving       │
    │ subsystem and an ARC track, the            │──── 810
    │ reconstituted reagent solution from the    │
    │ ARC track to the heating area              │
    └────────────────────┬───────────────────────┘
                         ▼
    ┌────────────────────────────────────────────┐
    │ Treating the reconstituted reagent solution│
    │ in the presence of the intermediate        │──── 812
    │ biomolecule, at the heating area, to       │
    │ produce a treated biomolecule              │
    └────────────────────┬───────────────────────┘
                         ▼
                    ┌──────────┐
                    │   End    │
                    └──────────┘
```

Figure 8

SYSTEMS AND METHODS RELATING TO PORTABLE MICROFLUIDIC DEVICES FOR PROCESSING BIOMOLECULES

RELATED APPLICATION

This application claims the benefit from International Application No. PCT/US2018/056961, which was granted an International filing date of Oct. 23, 2018, which in turns claims priority from U.S. provisional application No. 62/575,523, with a filing date of Oct. 23, 2017, which are incorporated herein by reference in its entirety for all purposes.

STATEMENT OF GOVERNMENT LICENSE RIGHTS

This invention was made with government support under Contract No. ECCS 1308025, awarded by the National Science Foundation. The government has certain rights in the invention.

FIELD

The present teachings and arrangements relate generally to microfluidic device systems that facilitate screening and sampling of biomolecules and other materials. More particularly, the present teachings and arrangements relate to field-deployable microfluidic devices and related systems that use Aniosotropic Ratchet Conveyor ("ARC") tracks that facilitate delivery of fluid droplets to microheaters and lyophilized reagents, disposed on a substrate containing an ARC track, to process biomolecules (e.g., DNA, RNA, and/or proteins), including but not limited to using isothermal DNA amplification for the purpose of species identification and/or validation.

BACKGROUND

Human-induced species extinction continues to accelerate. Several problems persist in threatening the survival of sensitive species. For example, the illegal wildlife and timber trade markets, worth billions of dollars, not only threaten the survival of many species, they also serve to hinder economic development and promote government and business corruption. As another example, illegal and unregulated fishing, as well as trafficking in marine products from threatened species, drive species extinction and deplete valuable resources at a rate that can not be recovered. As yet another example, introduction of invasive species into new ecosystems (e.g., as a result of illegal importation) can have a disastrous effect on survival of native species, and in the United States alone, is responsible for an estimated $12 billion per year in damage control costs.

Addressing such problems generally requires, in part, the ability to identify, screen, and/or sample various plant, marine, or animal species (e.g. at a border control checkpoint, in food samples, during on-site investigations, etc.). Conventional techniques for doing so suffer from certain infirmaries. For example, identification and screening of illegal timber and wildlife products and seafood are traditionally reliant on visual taxonomic identification, which requires highly trained personnel who can distinguish key features of closely related species, yet often lacks the necessary specificity for species identification. For timber, even microscopic analysis by experts can only reliably provide genus level identification. Additionally, many marine and wildlife species are also processed into products (e.g., filets, powders, ground meat, or oils) that further complicate visual identification. Similarly, detection and monitoring of invasive species is typically performed through traditional field studies relying on identification and sampling from visual or auditory encounters.

Other conventional approaches involve chemical analysis through mass spectrometry, near-infrared spectroscopy, DNA screening (e.g., polymerase chain reaction (PCR) techniques), and other laboratory techniques that require trained technical personnel and expensive laboratory equipment and materials and are not susceptible to portability and/or in-field use (e.g., at a border or other point of interception). And while certain of these techniques, such as PCR, provide increased sensitivity and accuracy, such sensitivity and accuracy comes at a cost and is generally not required to, for example, validate the presence of a species in a product, or to distinguish a species from known alternatives.

On the other hand, other conventional approaches that are inexpensive and that may be susceptible to in-field use, such as use of paper microfluidic devices, lack the requisite sensitivity and adaptability required for effective species identification or screening.

What is therefore needed are systems and methods that provide sufficiently accurate screening and sampling of, among other things, various plant, marine, and wildlife species, while remaining inexpensive and efficient, and at the same time, providing ease of use and portability to a non-technically trained end user.

SUMMARY OF THE INVENTION

In one aspect, the present teachings disclose a biomolecule processing device, which includes: (i) a substrate; (ii) a first anisotropic ratchet conveyor ("ARC") track defined on or within the substrate, with a biomolecule receiving area disposed on one end of the first ARC track; (iii) a heating area disposed at or near another end of the first ARC track, microfabricated with a microheater, which is designed to heat biomolecule that is received from the first ARC track; (iv) a second ARC track defined on or within the substrate, with a transport solution receiving area at or near one end and a reconstituting area at or near the other end, such that the transport solution receiving area is designed to receive transport solution, and the reconstituting area is designed to receive dry reagents and reconstitute dry reagents into reagent solution and/or suspension; (v) a third ARC track defined on or within the substrate, which intersects with the first ARC track and the first microheater on the second ARC track such that the third ARC track is designed to convey reconstituted reagent solution and/or suspension to the microheater area for processing. Each of the first ARC track, the second ARC track, and the third ARC track includes an arrangement of a plurality of hydrophilic rungs disposed on a hydrophobic region such that between two consecutive hydrophobic rungs, a portion of hydrophobic region is exposed.

The biomolecule processing device may also include a delivery junction that is disposed between the second ARC track and the third ARC track such that the delivery junction facilitates transport of the reconstituted reagent solution and/or suspension from the second ARC track to the microheater. The delivery junction includes one or more substantially linear hydrophilic guides that extend from the hydrophilic rungs of the second ARC track to the third ARC track. Preferably, the hydrophilic rungs are convex-shaped with a protruding portion extending in a direction towards the third ARC track, such that the substantially linear hydrophilic guides extend in a direction towards the third ARC track. In other words, the substantially linear hydrophilic guides are perpendicular to a plane or a line that tangentially intersects the protruding portion of the hydrophilic rung.

According to one embodiment of the present arrangements, the first ARC track and the second ARC track extend parallel to each other. According to another embodiment of the present arrangements, the third ARC track extends perpendicular to the first ARC track and the second ARC track.

In another aspect, the present teachings disclose another biomolecule processing device. The biomolecule processing device includes: (1) a first substrate, which includes: (a) an ARC track defined on or within the first substrate and that has a biomolecule receiving area, which is designed to receive biomolecule, and a reconstituting area, which is designed to contain dry reagents that will be reconstituted with transport solution; and (b) a first heating area disposed at or near the biomolecule receiving area, fitted with a first microheater, which is designed to heat biomolecule that is received through the biomolecule receiving area and designed to process heated biomolecule and dry reagents reconstituted with transport solution.

According to one preferred embodiment of the present arrangements, the biomolecule processing device also includes: (i) a gasket that does not completely surround the first microheater and that provides an aperture that is defined to receive the reagent solution and/or suspension; (ii) a second substrate, which includes: (a) a track defined on or within the second substrate; and (b) a second microheater area disposed at or near an end of the track, microfabricated with a second microheater. In an assembled state, the first substrate is disposed underneath the second substrate, the ARC track is opposite to and facing the track, the first microheater is opposite to and facing the second microheater, and the second microheater occupies a greater surface area than the first microheater. The track may be an ARC track or a hydrophobic coating, such as fluorooctyl-trichlorosilane (FOTS). Dry reagents may include temperature-sensitive materials (e.g., polymerase). Preferably, the ARC track includes an arrangement of a plurality of hydrophilic rungs disposed on a hydrophobic region such that between two consecutive hydrophilic rungs, a portion of hydrophobic region is exposed.

In yet another aspect, the present teachings disclose a biomolecule processing system. The biomolecule processing system includes: (i) a vibration-driving subsystem that is configured to deliver orthogonal vibration waves to a substrate; and (ii) a biomolecule processing device coupled to the vibration-driving subsystem, which includes: (i) a substrate; (ii) an ARC track defined on or within the substrate, with a biomolecule receiving area, which is designed to receive biomolecule, and a reconstituting area, which is designed to contain dry reagents and is designed to receive a transport solution such that at the reconstituting area, dry reagents are reconstituted with transport solution; (iii) a microheater area disposed at or near the biomolecule receiving area, fitted with a microheater, which is designed to heat biomolecule that is received through the biomolecule receiving area and designed to process heated biomolecule and dry reagents reconstituted with transport solution.

In another aspect, the present teachings disclose a method for processing biomolecule. The process includes: (i) receiving a biomolecule at or near a biomolecule receiving area; (ii) receiving a transport solution at or near a transport solution receiving area; (iii) conveying, using a vibration-driving subsystem that delivers orthogonal vibration signals, the biomolecule along a first ARC track to a heating area, and the transport solution along a second ARC track to a reconstituting area; (iv) heating, at the heating area, the biomolecule to produce an intermediate biomolecule; (v) reconstituting, at the reconstituting area, the transport solution in the presence of one or more dry reagents to produce a reconstituted reagent solution and/or suspension; (vi) delivering, using a delivery junction and the vibration-driving subsystem, the reconstituted reagent solution and/or suspension from the second ARC track to a third ARC track; (vii) advancing, using the vibration-driving subsystem, the reconstituted reagent solution and/or suspension from the third ARC track to the heating area; and (viii) processing, at the heating area, the reconstituted reagent solution and/or suspension in the presence of intermediate biomolecule to produce a processed biomolecule. The processed biomolecule may produce amplified DNA. According to one embodiment of the present arrangements, during conveying, the vibration-driving subsystem delivers orthogonal vibration signals at a first frequency, during delivering, the vibration-driving subsystem delivers orthogonal vibration signals at a second frequency, and during advancing, the vibration-driving subsystem delivers the orthogonal vibration signals at the first frequency.

The delivery junction is configured to pause the reconstituted reagent and/or suspension during conveying.

In certain embodiments of the present arrangements, conveying, delivering, and/or advancing is carried out on a tilted substrate that is disposed at an angle, relative to a flat and horizontal surface, that is between about 5° and about 15°.

In yet another aspect, the present teachings disclose another method for processing biomolecule. The regimen includes: (i) receiving a biomolecule at or near a biomolecule receiving area that is located on or near a heating area that has a microheater; (ii) receiving a transport solution at or near a transport solution receiving area that is also a reconstituting area that includes lyophilized reagents; (iii) heating the biomolecule at the heating area to produce an intermediate biomolecule; (iv) reconstituting the transport solution, at the reconstituting area, in the presence of one or more dry reagents to produce a reconstituted reagent solution and/or suspension; (v) conveying, using a vibration-driving subsystem and an ARC track, the reconstituted reagent solution and/or suspension from the ARC track to the heating area; and (vi) processing the reconstituted reagent solution and/or suspension at the heating area and in the presence of the intermediate biomolecule to produce a processed biomolecule. The processed biomolecule may produce or otherwise include amplified DNA.

According to one embodiment of the present teachings, heating is carried out at a temperature that is about 95° C. and produced lysed (released) biomolecule. According to another embodiment of the present teachings, processing includes carrying out isothermal DNA amplification at a temperature that is about between about 65° C. and about 70° C., and more preferably, about 65° C., to produce amplified DNA. Such processing may include loop-mediated isothermal DNA amplification to produce amplified DNA product. The amplified DNA product may be analyzed to confirm the identity of a plant or animal species from which the biomolecule sample was obtained.

In yet another aspect, the present teachings disclose a process for species identification and/or validation. The process includes: (i) receiving a sample containing DNA on an ARC track defined on a substrate or at a microheater connected to the ARC track; (ii) lysing the sample containing DNA at or on the microheater at a temperature that is between about 90° C. and about 100° C. to produce lysed sample; (iii) reducing the temperature to between about 60° C. and about 75° C.; (iv) delivering, on the ARC track, a buffer with reagents to the microheater to mix with the lysed sample to produce a processed sample; (v) performing isothermal DNA amplification on the processed sample to produce amplified DNA; and analyzing the amplified DNA to carry out species identification. Analyzing the DNA sample may include at least one member selected from a group comprising: validating presence of species source of the sample containing DNA, determining species source of the sample containing DNA, and distinguishing species source of the sample containing DNA from known alternatives. Preferably, performing isothermal DNA amplification includes performing loop-mediated DNA amplification on the processed sample.

In certain embodiments of the present teachings, prior to lysing, the sample containing DNA is conveyed, along the ARC track, to the microheater.

Systems and methods of the present teachings and arrangements, however, together with additional objects and advantages thereof, will be best understood from the following descriptions of specific embodiments when read in connection with the accompanying figures.

BRIEF DESCRIPTION OF THE DRAWINGS

FIG. 8 is a flowchart showing certain salient steps of a method for carrying out biomolecule processing, according to one embodiment of the present teachings.

DETAILED DESCRIPTION OF THE PREFERRED EMBODIMENTS

In the following description, numerous specific details are set forth in order to provide a thorough understanding of the present arrangements and teachings. It will be apparent, however, to one skilled in the art that the present teachings may be practiced without limitation to some or all of these specific details. In other instances, well-known process steps have not been described in detail in order to not unnecessarily obscure the present teachings.

The systems and methods of the present arrangements and teachings recognize that when vertical, or orthogonal, vibrations are applied to a fluid droplet resting on a substrate, axisymmetric waves will form along the surface of the droplet. Once of sufficient amplitude, the vibrations will cause a contact line of the droplet (i.e., the perimeter of the droplet in contact with the substrate) to oscillate. Each oscillation cycle is composed of two phases: an expansion phase and a contraction phase. A droplet oscillating on a homogeneous substrate enters the expansion phase when the contact line is at its smallest circumference. The contact line then advances in all directions throughout this phase. During the contraction phase, the contact line starts at its largest circumference and recedes until the next expansion phase begins. Contact line driven microfluidic systems utilize surfaces that introduce an asymmetry to this oscillation cycle. Such systems move droplets through an imbalance of pinning forces (i.e., contact force associated with contact of a droplet with hydrophilic regions on a substrate surface) on the edges of the contact line. Contact line driven microfluidic transport is described in more detail in U.S. Pat. No. 9,279,435B2, which is incorporated herein by reference.

Figure 1A:
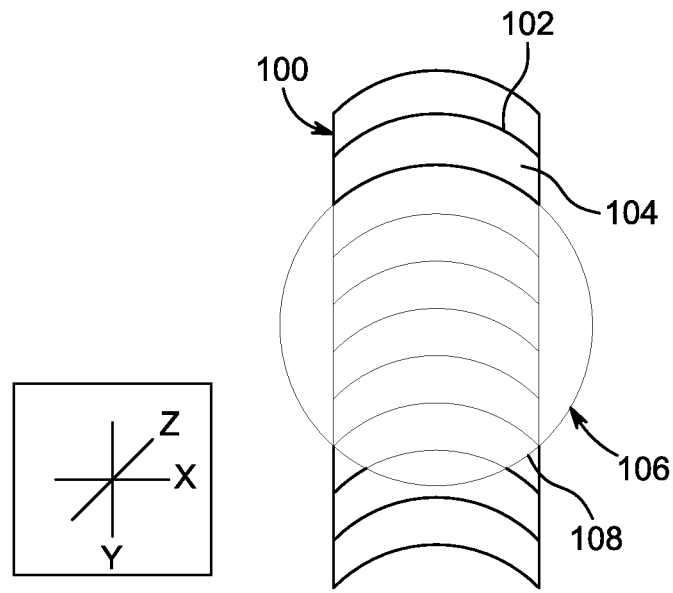
FIG. 1A is top view of an exemplar ARC track, according to one embodiment of the present arrangements and with a fluid droplet in a state of equilibrium disposed thereon.

One example of a contact line driven digital microfluidic surface is anisotropic ratchet conveyors ("ARCs"), or ARC tracks, that are fabricated on a substrate and which facilitate microfluidic transport along their surface patterns. FIG. 1A shows an exemplar ARC track 100, according to one embodiment of the present arrangements. ARC track 100 includes a plurality of hydrophilic rungs 102 alternating, one at a time, between a plurality of hydrophobic regions or borders 104. Put another way, ARC track 100 includes an arrangement of a plurality of hydrophilic rungs 102 and a plurality of hydrophobic regions 104 such that in a space between two consecutive hydrophilic rungs, one hydrophobic region is defined.

FIG. 1A also shows a fluid droplet 106, with a contact line 108, disposed on ARC track 100. Droplet 106 may be thought of as being in a state of equilibrium, where little or no vibrational energy is being supplied, so little or no motion or oscillation of droplet 106 is generated.

According to preferred embodiments of the present arrangements, rungs 102 are hydrophilic. The present teachings recognize that the hydrophobic nature of borders 104 keeps droplet 106 predominantly confined to ARC track 100 during transport.

ARC tracks of the present arrangements may be considered textured or chemical based, depending on how they are fabricated on a substrate. For textured ARC tracks, rungs are patterned mesas surrounded by a trench, and hydrophobic regions are created by an array of pillars. Preferably, textured ARC tracks are created by etching.

Chemical ARC tracks, on the other hand, are comprised of alternating hydrophobic borders and hydrophilic rungs on a flat surface that are created by chemical deposit. Preferably, chemical-based ARC tracks use hydrophilic rungs comprised of $SiO_2$. While the systems and methods of the present arrangements and teachings recognize that either textured ARCs or chemical-based ARCs may be used to practice the present inventions, chemical-based ARC tracks represent a preferred embodiment of the present inventions. A representative process for fabricating a chemical-based ARC track is set forth below in Example 1.

Arcs or rungs 102 may be characterized as having a "period" (i.e., a spacing interval distance between successive rungs) and a width, or a thickness. According to one embodiment of the present arrangements, rungs 102 have a period of about 60 μm. According to another embodiment of the present arrangements, rungs 102 have a period of about 120 μm. According to yet another embodiment of the present arrangements, rungs 102 have a period of between about 15 μm and about 240 μm.

Preferably, rungs 102 have a width, or a thickness, that is between about 0.5 μm and about 20 μm. According to one embodiment of the present arrangements, rungs 102 have a width that is about 5 μm. According to another embodiment of the present arrangements, rungs 102 have a width that is about 10 μm.

With respect to ARC track 100, using values for period and width, a duty cycle may be calculated, where a duty cycle is the width of rungs 102 divided by the period of rungs 102, expressed as a percentage. According to one embodiment of the present arrangements, ARC track 100 has a duty cycle of about 8.3%. According to another embodiment of the present arrangements, ARC track 100 has a duty cycle that is about 16.6%. According to yet another embodiment of the present arrangements, ARC track 100 has a duty cycle that is between about 2.5% and about 50%.

The present teachings recognize that on a single ARC track, duty cycles of different values may be used to manipulate transport of a droplet, as transport velocity of a droplet on an ARC pattern is influenced by duty cycle. For example, the present teachings recognize that duty cycles of relatively higher values require additional vibrational energy to advance along an ARC track. Accordingly, a single ARC track may be comprised of adjacent areas having higher (e.g., about 16.6%) and lower (e.g., about 8.3%) duty cycles, such that without supplying additional vibrational energy, a fluid droplet may be prevented from advancing onto or along an ARC track from an area having a lower duty cycle to an area having a higher duty cycle value. In such manner, a fluid droplet may be thought of as paused on the ARC track. A region on an ARC track that uses changes in duty cycle to selectively pause microfluidic transport may be thought of as an "ARC gate."

Rungs 102 have a rung radius that is a value between about 250 μm and about 2500 μm, and more preferably, about 1000 μm.

As the ARC tracks of the present arrangements provide for continuous transport, there are no constraints on the length of ARC track 100. A width of ARC track 100 is determined by the sector of curved rung 102. Preferably, a sector of curved rung 102 has a value that is between about 90° and about 180°.

Figure 1B:
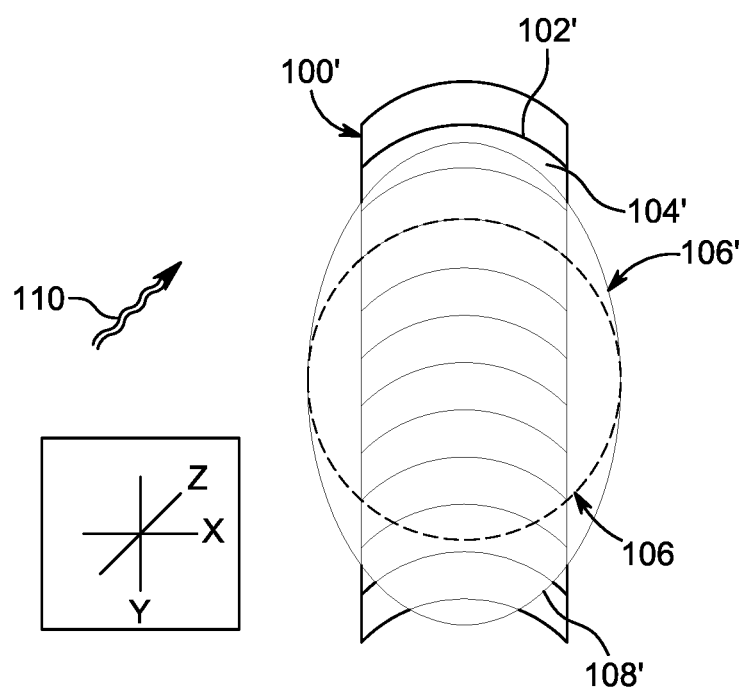
FIG. 1B is top view of the exemplar ARC track of FIG. 1A, according to another embodiment of the present arrangements and with a fluid droplet oscillating in both directions due to supplied vibrational energy.

FIG. 1B shows an ARC track 100', according to another embodiment of the present arrangements, with alternating rungs 102' and hydrophobic borders 104', and a droplet 106 (depicted with dashed lines), which are substantially similar to their counterparts in FIG. 1A, i.e., ARC track 100, alternating rungs 102 and hydrophobic borders 104, and droplet 106. FIG. 1B also shows a droplet 106' with a contact line 108', as well as vibrational energy 110.

FIG. 1B shows the effect, on droplet 106 of FIG. 1A, of supplied orthogonal vibrational energy 110 to ARC track 100. To this end, FIG. 1B shows expansion of droplet 106' (i.e., compared to droplet 106 of FIG. 1A, depicted with dashed lines in FIG. 1B), due to oscillation. As mentioned above, expansion of contact line 108' increases the area of the substrate that is in contact with droplet 106', which is referred to as the "wetting" phase, or the "expansion" phase. The present teaching recognize that expansion from droplet 106 of FIG. 1A to droplet 106' of FIG. 1B is relatively symmetrical (i.e., contact line 108' expands relatively equally in both directions along the y axis in FIG. 1B, as the wetting process is relatively insensitive to ARC surfaces).

Vibrational energy 110 is supplied to ARC track 100' vertically, or orthogonically (i.e., along the z axis, as shown in FIG. 1B). Vibrational energy 110 may be delivered by any means well known to those of skill in the art. By way of example, vibrational energy 110 is delivered by at least one member selected from a group comprising an electromagnetic motor, a solenoid, and a piezoelectric oscillator. Preferably, vibrational energy is delivered to ARC track 100' at a value that is between about 10 Hz and about 500 Hz, and more preferably, at a resonant frequency. The present teachings recognize that a resonant frequency of an ARC track depends on both droplet volume and other liquid properties (e.g., density) of a droplet, as well as the ARC pattern (e.g., duty cycle) of an ARC track. According to one embodiment of the present teachings, a displacement of vibration amplitude delivered to ARC track 100' has a value that is between about 100 μm and about 2 mm.

Figure 1C:
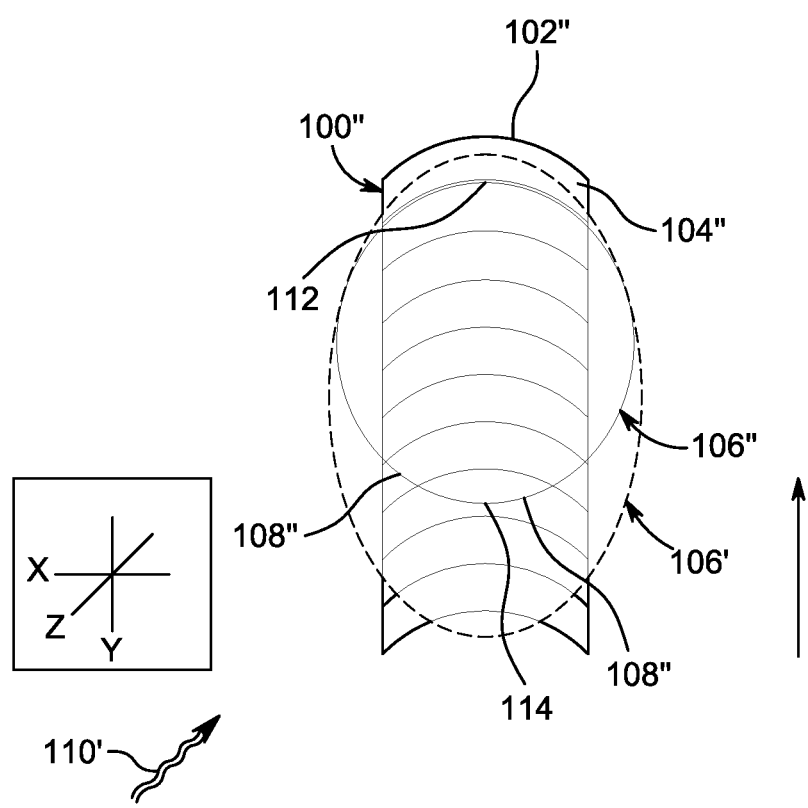
FIG. 1C is top view of the exemplar ARC track of FIGS. 1A and B, according to yet another embodiment of the present arrangements and showing a fluid droplet advancing along the ARC track in one direction.

FIG. 1C shows an ARC track 100", according to another embodiment of the present arrangements, with alternating rungs 102" and hydrophobic borders 104", which are substantially similar to their counterparts in FIG. 1B, rungs 102' and borders 104', alternating one by one. Fluid droplet 106" and vibrational energy 110' are likewise substantially similar to their counterparts in FIG. 1B, i.e., fluid droplet 106' (depicted with dashed lines in FIG. 1C) and vibrational energy 110.

FIG. 1C also shows a droplet 106" with a leading edge 112 and a trailing edge 114, as well as a contact line 108". Droplet 106" may be thought of as the same as droplet 106" of FIG. 1B, after the droplet has contracted due to oscillation. Leading edge 112 may be thought of as the front portion of contact line 108" that advances along ARC track 100", while trailing edge 114 may be thought of as the back portion of contact line 108' that advances along track 100", during such contraction. The arrow shown parallel to ARC track 100' in FIG. 1C shows the direction of movement of fluid droplet 106" on ARC track 100", along the y-axis. Direction of movement of a fluid droplet along an ARC track may be thought of as the same as or substantially similar to the direction rungs point along an ARC track.

The present teachings recognize that the asymmetric ARC surface pattern depicted in FIGS. 1A-1C creates a difference in pinning forces between leading edge 112 and trailing edge 114. Pinning forces associated with leading edge 112 are stronger due to the leading edge's conformance to the curvature of hydrophilic rungs 102". This imbalance of forces results in net transport along ARC track 100", along the direction of ARC rungs 102", during each vibration cycle. In other words, vibrational energy applied to an ARC track causes the contact line of a droplet to oscillate, promoting fluid movement along a path of hydrophilic rungs in the direction ARC rungs.

The present teachings recognize that microfluidic transport on ARC tracks is the result of two key factors. The first is a difference in pinning forces between leading and trailing edges of the droplet, which is provided for by an asymmetric surface pattern of periodic, curved rungs. As shown in in FIGS. 1A-1C, this pattern is composed of alternating hydrophilic and hydrophobic regions, where the rungs are hydrophilic and defined by a hydrophobic background. Pinning is the interaction of the droplet edges with the hydrophilic regions, and can be thought of as a frictional force, as pinning resists the movement of droplet edges. Droplets resting on this pattern will maintain a spherical shape because of their surface tension, allowing only the leading edge to conform to the curvature of the hydrophilic rungs to create this difference in pinning forces.

The second feature is the oscillation of droplet edges, which is typically induced by an applied orthogonal vibration to the substrate. Vibrations cause the droplet edges to expand and contract, cycling the droplet through phases of wetting—i.e., droplet edges advancing on the substrate—and de-wetting—i.e., droplet edges receding from the substrate. Combining this oscillation of droplet edges with a difference in pinning forces between edges produces a net force in the direction of the leading edge throughout one vibration cycle (e.g., as shown in FIGS. 1A-1C). In other words, the droplets will take a step forward throughout each vibration cycle. Over the course of many vibration cycles, these steps provide for the propulsion or net transport of the droplets along an ARC track.

For droplets on ARC tracks, there is a minimum vibration amplitude, i.e., the ARC threshold, required to initiate transport of a fluid droplet thereon. The present teachings recognize that this amplitude is determined by the geometry and/or chemical composition of the ARC track, physical properties of the transported droplet, as well as the frequency and waveform of the applied vibration. ARC threshold profiles effectively describe the performance of an ARC device with a specific droplet and are collected across a functional frequency range. At frequencies outside of this range, transport is not possible as droplets will either bounce off the substrate or rupture before transport occurs. For vibration amplitudes above the ARC threshold, transport will still occur until the amplitude is so high as to cause the droplet to completely depin (bounce off) of the substrate or rupture. However, these amplitudes are typically high within the functional frequency range.

Figure 2:
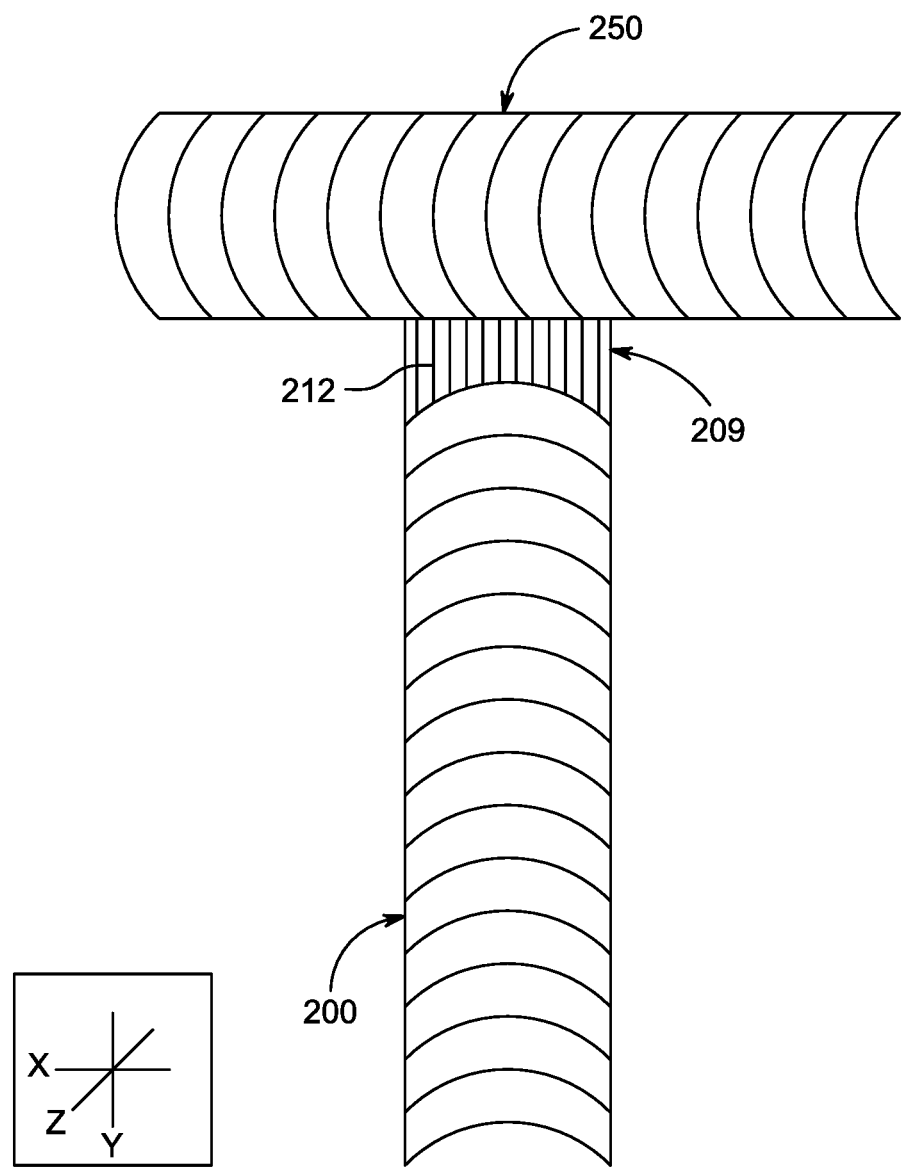
FIG. 2 is a top view of one exemplar ARC track connected to another exemplar ARC track by a delivery junction, according to one embodiment of the present arrangements.

While FIGS. 1A-1C show advancement of a fluid droplet along a single exemplar ARC track, the present teachings recognize that certain other features are useful in manipulating movement of a fluid droplet between ARC tracks. To this end, FIG. 2 shows perpendicular ARC tracks connected by a delivery junction, according to one embodiment of the present arrangements. An ARC track 200 and an ARC track 250 are substantially similar to their counterpart in FIG. 1A, i.e., ARC track 100. FIG. 2 also shows a delivery junction 209 with hydrophilic guides 212 extending thereon in the same direction as ARC track 200. Put another way, delivery junction 209 includes one or more substantially linear hydrophilic guides 212 that extend from the hydrophilic rungs of ARC track 200 to ARC track 250. As shown in FIG. 2, the hydrophilic rungs of ARC track 200 are convex-shaped with a protruding portion extending in a direction towards ARC track 250 such that the substantially linear hydrophilic guides 212 extend in the same direction towards ARC track 250. In other words, substantially linear hydrophilic guides 212 are perpendicular to a plane or a line that tangentially intersects the protruding portion of hydrophilic rungs on ARC track 200.

Delivery junction 209 may be thought of as a region connected to ARC track 202 that is configured to transfer droplet 202 to ARC track 204 without impeding transport. To this end, hydrophilic guides 212 extend within delivery junction 209 such that the hydrophilic guides, during fluid transport thereon, carefully balance pinning forces associated with a fluid droplet's movement to transition the droplet from ARC track 200 to ARC track 250, without leaving it stuck on the delivery junction. While wishing not to be bound by theory, it is thought that hydrophilic guides 212 promote delivery of a droplet from the terminated track (i.e., ARC track 200) by wicking or pulling the droplet edge towards the main track (i.e., ARC track 250). When paired with the correct vibration signal, pinning forces on the main track will overtake the droplet from the terminating track.

Preferably, the distance defined between ARC track 200 and ARC track 250, by delivery junction 209, is a value that is between about 500 µm and about 2000 µm, and more preferably, between about 1015 µm and about 1115 µm.

The ability to manipulate droplet movement along and between ARC tracks provides powerful tools useful for sampling, screening, and/or processing various components susceptible to microfluidic transport. In particular, the present teachings recognize that processing of biomolecules, i.e., DNA, RNA, or protein, may be carried out ARC-based processing devices. Further, adaptations to such devices, as explained below, provide certain advantages in carrying out biomolecule processing. As one example, fabrication of a microheater that is on or connects to an ARC track provides means for carrying out in thermal processing steps on a biomolecule sample (e.g., cellular lysis and/or isothermal DNA amplification). As another example, reagents or other materials used in such thermal processing may be dried, or lyophilized, on an ARC track, delivery junction, and/or microheater, where such reagents and/or other materials may be reconstituted and delivered to a microheater for use in certain processing steps.

Figure 3A:
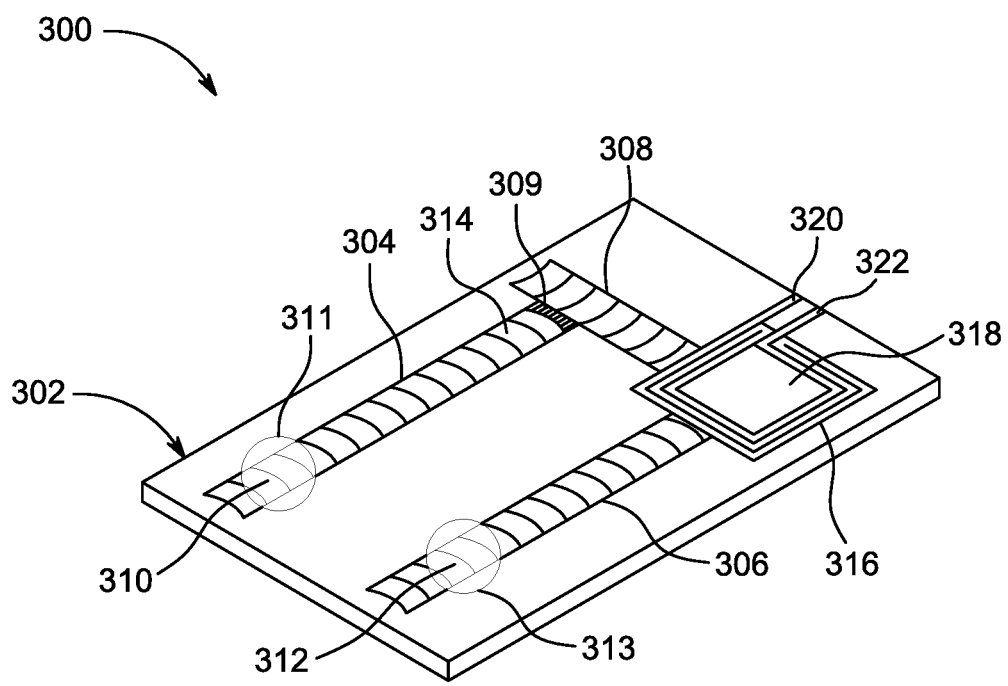
FIG. 3A is a perspective view of an ARC-based biomolecule processing device, according to one embodiment of the present arrangements and showing a biomolecule sample droplet disposed at a biomolecule sample receiving area and a transport solution droplet disposed on a transport solution receiving area.

FIG. 3A shows a perspective view of an ARC-based biomolecule processing device 300, according to one embodiment of the present arrangements. Device 300 includes a substrate 302, an ARC track 304, an ARC track 306, an ARC track 308, a delivery junction 309, a transport solution receiving area 310, a biomolecule sample receiving area 312, a reconstituting area 314, a microheater 316, a heating area 318, a first lead end 320, and a second lead end 322. FIG. 3A also shows a transport solution droplet 311 disposed on transport solution receiving area 310 and a biomolecule sample droplet 313 disposed on biomolecule sample receiving area 312.

Substrate 302 is any substrate capable of having one or more ARC tracks microfabricated thereon. Preferably, substrate 302 is comprised of glass, and more preferably, is a transparent soda-lime glass wafer. A representative process for fabricating a substrate using a soda-lime glass wafer is set forth in Example 2. According to another embodiment of the present arrangements, substrate 302 is single crystal silicon.

The present teachings recognize certain advantages to the use of glass substrates, or wafers, in the ARC-based bioprocessing devices of the present arrangements. In particular, glass provides superior thermal insulation over other materials, such as silicon. As explained in further detail below, this feature of glass allows localization of high-temperature processing (e.g., by microheater 316 at heating area 318) to a particular substrate region without substantial heating of other substrate regions (i.e., where temperature-sensitive material may be lyophilized, such as reconstituting area 314). In other words, heating remains localized to the heating area where microheater 316 is disposed. This provides the advantage of using the present ARC device to carry out high-temperature processing of samples at heating area 318, while protecting temperature-sensitive materials located or disposed elsewhere on substrate 302 until such temperature-sensitive materials are delivered to heating area 318 for lower-temperature processing.

Further, glass wafers, because they are transparent, facilitate optical detection of processing results (e.g., presence of DNA amplicons) visually or by use of a camera.

Further still, glass wafers are relatively inexpensive and thus are appropriate for disposal/recycling after a single use.

A length and a width of substrate 302 may be adjusted to suit the needs of specific circumstances of use. By way of example, a surface area of substrate 202 may be adjusted to accommodate configurations that, unlike the embodiment of FIG. 3A, utilize fewer or more ARC tracks, ARC tracks of varying configuration, and/or other or more sub-components. According to one embodiment of the present arrangements, substrate 202 has a has a length that is between about 0.5 cm and about 3 cm, According to another embodiment of the present arrangements, substrate 202 has a width of about 0.15 cm. According to yet another embodiment of the present arrangements, substrate 302 has a thickness that is between about 400 μm and about 700 μm, and preferably, about 550 μm.

Like ARC track 100 described above with reference to FIG. 1A, ARC track 204, ARC track 206, and ARC track 208 are elongated tracks microfabricated onto substrate 202 as a pattern of transverse arcuate regions that facilitate transport of microfluids (e.g., fluid droplets) thereon by. According to preferred embodiments of the present arrangements, ARC tracks 302, 304, and 306 are $SiO_2$ ARC tracks having a pattern of $SiO_2$ rungs (e.g., rungs 102 of FIG. 1A) defined by hydrophobic intermediate regions therebetween. Preferably, the hydrophobic intermediate regions are comprised of fluorooctyltrichlorosilane (FOTS) that is coated onto substrate 302.

As shown in FIG. 3A, ARC track 304 includes, at one end, transport solution receiving area 310 with transport solution droplet 311 disposed thereon. Transport solution receiving area 310 may be thought of as a region on ARC track 304 where transport solution is delivered by a user (e.g., by use of a pipet, eyedropper, or the like). Transport solution 311 may be any fluid or buffer that the present systems may use to reconstitute downstream materials and reagents for later processing (e.g., at heating area 318). According to one embodiment of the present arrangements, transport solution includes at least one member chosen from a group comprising: acetic acid/sodium acetate; ammonium chloride/ammonia; bicarbonate/carbon dioxide (carbonic acid); hydrogen phosphate/biphosphate; citric acid/citrate; hydroxymethyl aminomethane; and sodium dodecyl sulfate.

According to one embodiment of the present arrangements, a transport solution fluid droplet has a volume that is between about 1 μL and about 25 μL, preferably between about 8 μL and about 13 μL, and more preferably, about 10 μL.

Though the embodiment of FIG. 3A shows transport solution receiving area 310 located at one end of ARC track 304, the present teachings recognize that transport solution receiving area 310 may be located along any portion of any ARC track, delivery junction, or microheater.

ARC track 304 also includes reconstituting area 314 at one end. Reconstituting area 314 is characterized by having certain material useful for downstream processing lyophilized, or dehydrated, thereon. Materials lyophilized at reconstituting area 314 may be temperature-sensitive reagents used in downstream heat-processing steps by the present ARC-based biomolecule processing devices. According to one embodiment of the present arrangements, materials lyophilized at reconstituting area 314 include at least one member selected from a group comprising ionic salt, chaotropic salt, polymerase, dNTP, molecular probe, fluorescent stain, antibody, blocking protein, nuclease enzymes, protease enzymes, and surfactant. The present teachings recognize that other areas on substrate 302 may be used as a reconstituting area. For example, reagents or other materials may be lyophilized along any portion of an ARC track, a delivery junction, or at or near a microheater.

The present teachings recognize that lyophilizing materials at reconstituting area 314 provides key efficiency advantages, rendering the present systems amenable to in-field use by a non-technically trained end user. In particular, because materials are lyophilized on substrate 302 prior to use of the ARC-based devices in-field, the end-user, who may not be technically trained, avoids carrying out the precise and time-consuming steps of aliquoting or otherwise distributing various materials at quantities required for biomolecule processing. In other words, the end-user need not be trained or competent in molecular biology laboratory techniques in order to use the present systems for biomolecule processing.

ARC track 306, at one end, has a biomolecule sample receiving area 312 with a biomolecule sample droplet 313 disposed thereon. Biomolecule receiving area 312 may be thought of as a location on substrate 302 where a biomolecule sample to be processed is introduced to system 300 (e.g., by using a pipet or an eyedropper). A biomolecule sample may be thought of as any biological sample containing DNA, RNA, or protein for processing by the present system, suspended in fluid and/or in solution.

The present teachings also recognize, however, that the ARC devices of the present teachings may be used or adapted to facilitate processing, screening, sampling, and/or analysis of non-biological material, such as heavy metals, toxins, and pollutants.

While the embodiment of FIG. 3A shows biomolecule sample receiving area 312 disposed on one end of ARC track 306, the present teachings recognize that a biomolecule receiving area may be located on any portion of substrate 312. According to one embodiment of the present arrangements, biomolecule sample receiving area 312 is located on or near microheater 316. According to such embodiments, microheater 316 may include certain materials or components lyophilized thereon. Such materials or components will be reconstituted in biomolecule sample droplet 313 due to heating steps carried out at heating area 318, supplied vibration, and/or diffusion.

According to one embodiment of the present arrangements, a biomolecule sample fluid droplet has a volume that is between about 1 µL and about 25 µL, preferably between about 8 µL and about 13 µL, and more preferably about 10 µL.

FIG. 3A also shows a delivery junction 309 disposed between ARC track 304 and ARC track 308. Delivery junction 309 is substantially similar to delivery junction 209, described above with reference to FIG. 2.

FIG. 3A shows microheater 316 microfabricated on substrate 302. According to the embodiment of FIG. 3A, microheater 316 is coupled on one side to ARC track 308 (i.e., to facilitate delivery of droplet 311 to heating area 318) and on another side to ARC track 306 (i.e., to facilitate delivery of droplet 313 to heating area 318). Heating area 318 may simply be thought of as an area within, on, and/or surrounding microheater 318 where heat is delivered at a desired temperature to process a biomolecule sample fluid droplet, a transport fluid solution droplet, one or more reagents dissolved or resuspended in a biomolecule sample fluid droplet or a transport fluid solution droplet, and/or any mixture of such fluid droplets and/or reagents.

Microheater 316 may be comprised of any material or materials capable of converting energy to heat for use in heating process steps contemplated by the present teachings. According to one preferred embodiment of the present arrangements, microheater 316 is comprised of molybdenum. According to other embodiments of the present arrangements, microheater 316 is comprised of at least one member selected from a group comprising aluminum, gold, chromium, silver, copper, tungsten, iron, or platinum. Preferably, the region on or near microheater 316, including heating area 318, is hydrophilic. According to one embodiment of the present arrangements, the region on or near microheater 316, including heating area 318 is coated with surfactant.

As shown in the embodiment of FIG. 3A, microheater 316 is constructed from a lead (preferably a molybdenum lead) that forms the microheater through a triple winding into the shape of a square, with lead ends 318 and 320 extending to an edge of substrate 302. The present teachings, however, contemplate use of any number of windings to construct the microheaters of the present teachings. According to an alternate embodiment of the present arrangements, microheater 316 is constructed, in the shape of a square, with a single winding of a molybdenum lead. The present teachings also contemplate use of microheaters of varying shapes.

According to one embodiment of the present arrangements, a molybdenum lead used to construct microheater 316 has a thickness, or depth, that is between about 200 nm and about 500 nm, and preferably, about 350 nm. Characterization of various exemplar microheaters of varying lengths (i.e., windings) and widths is shown below in Example 3.

As shown in FIG. 3A, lead ends 320 and 322 abut an edge of substrate 302. The present teachings recognize that lead ends 320 and 322 are used to couple microheater 316 to a power source and other associated components necessary to control delivery of energy to microheater 316 for heating.

Figure 3B:
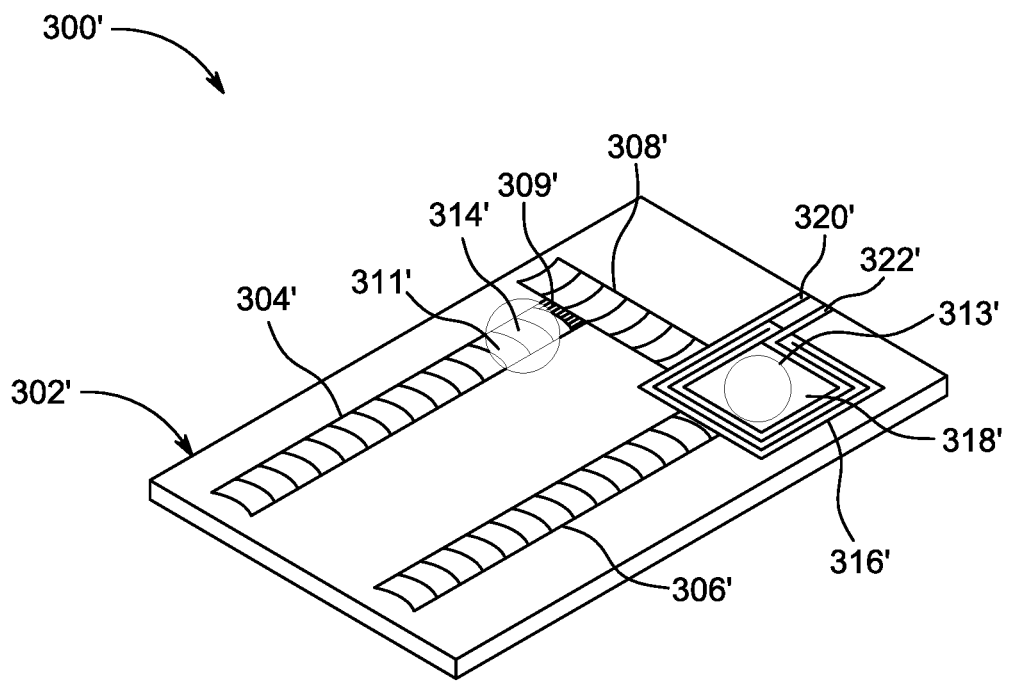
FIG. 3B is a perspective view of the ARC-based biomolecule processing device of FIG. 3A, according to one embodiment of the present arrangements and showing a transport solution droplet disposed at a reconstituting area and a biomolecule sample droplet disposed at a heating area.

FIG. 3B shows a perspective view of an ARC-based biomolecule processing device 300', according to another embodiment of the present arrangements. A substrate 302', an ARC track 304', an ARC track 306', an ARC track 308', a delivery junction 309', a transport solution droplet 311', a biomolecule sample droplet 313', a reconstituting area 314', a microheater 316', a heating area 318', a first microheater lead end 320', and a second microheater lead end 322', are substantially similar to their counterparts in FIG. 1A, i.e., substrate 302, ARC track 304, ARC track 306, ARC track 308, delivery junction 309, transport solution droplet 311, biomolecule sample droplet 313, reconstituting area 314, microheater 316, heating area 318, first microheater lead end 320, and second microheater lead end 322. Device 300' may be thought of as the same as device 300, after vibrational energy has been supplied to facilitate advancement of fluid droplets (e.g., fluid droplets 311 and 313) to different locations thereon.

In particular, FIG. 3B shows transport solution droplet 311' disposed on reconstituting area 314'. As mentioned above with reference to FIG. 3A, a reconstituting area may include certain lyophilized materials and/or reagents. When transport solution droplet 311' has advanced to, or is otherwise deposited on, reconstituting area 314', those materials and/or reagents may be reconstituted therein. Reconstitution of reagents and/or materials into a reconstituted reagent solution and/or suspension may be facilitated by supply of vibrational energy to the substrate.

Delivery junction 309' is used to facilitate delivery of transport solution 311' from ARC track 304' to ARC track 308'. Delivery junction 309' may also be used to selectively pause delivery of transport solution 311' thereon. The present teachings recognize that two thresholds exist for a delivery junctions: a "pass" threshold, i.e., the vibration amplitude required for a droplet to travel on a main track and pass the hydrophilic guides without getting stuck, and the "deliver" threshold, i.e., the vibration amplitude required to transfer a droplet from the terminating track onto the main track. Thus, vibrational energy supplied to substrate 302' may be set to a pass threshold, which will pause advancement of transport solution 311' at the delivery junction 309' until vibrational energy is adjusted to a deliver threshold. In such manner, the present arrangements may be used to selectively pause transport of microfluids at or near a delivery junction. The present teaching further recognize that ARC gates may be used on other areas of ARC tracks to promote the same effect of selectively pausing microfluid transport.

In certain embodiments of the present arrangements, reagents and or other materials are lyophilized on delivery junction 309' for reconstitution in transport solution.

FIG. 3B also shows biomolecule sample 313' disposed on heating area 318', which is preferably located on, within, or around microheater 318'. Heating area 318' and microheater 316' are preferably hydrophilic to facilitate stabilization or resting of microfluids thereon.

The present teaching recognize that fluid droplets 311' and 313' may be advanced from areas 310' and 312', respectively, in parallel. In other words, droplets 311' and 313' may be advanced by a single supply of vibrational energy to substrate 302'. As shown in FIG. 2A, however, while droplet 313' is located at heating area 318', droplet 311' remains paused, or stopped, at reconstituting area 314'. The present teachings recognize that delivery junction 309' has an ARC threshold that must be exceeded to deliver droplet 311' to arc track 310. If this ARC threshold is not met, delivery of the fluid droplet to the ARC track is paused. Additional vibrational energy must then be supplied to exceed this ARC threshold for delivery to a subsequent ARC track. Pausing droplet 311' in such manner allows droplet 313' to be subjected to thermal processing (e.g., biomolecule sample lysis) without subjecting droplet 311' to the same the same thermal processing step.

Figure 3C:
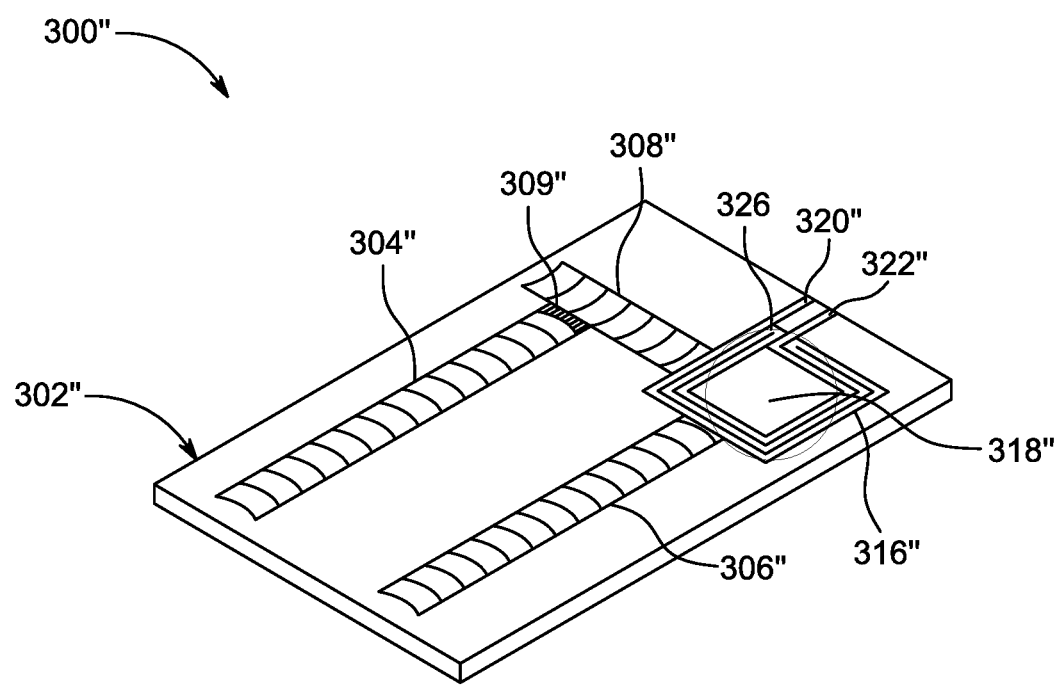
FIG. 3C is a perspective view of the ARC-based biomolecule processing device of FIGS. 3A and 3B, according to one embodiment of the present arrangements and showing a biomolecule sample and a transport solution mixture disposed at a heating area.

FIG. 3C shows a perspective view of an ARC-based biomolecule processing device 300", according to another embodiment of the present arrangements. The embodiment of FIG. 3C may be thought of as the same as or substantially similar to the embodiments of FIGS. 3A and 3B, though the embodiment of FIG. 3C also shows a droplet mixture 326 located at heating area 318". Droplet mixture 326 may be thought of as a mixture of droplets 311' and 313', as shown in FIG. 3B, on heating area 318". In certain embodiments of the present arrangements, either or both of droplets 311' and 313' is subject to treatment steps prior to mixing at heating area 318".

A substrate 302", an ARC track 304", an ARC track 306", an ARC track 308", a delivery junction 309", a microheater 316", a heating area 318", a first lead end 320", and a second lead end 322", are substantially similar to their counterparts in FIG. 2B, i.e., substrate 302', ARC track 304', ARC track 306', ARC track 308', delivery junction 309', microheater 316', heating area 318', first lead end 320', and second lead end 322'.

The present teaching recognize that mixture of the transport solution (i.e., reconstituted reagent solution and/or suspension) and the biomolecule sample may be facilitated by supplying vibrational energy to substrate 302".

Figure 4:
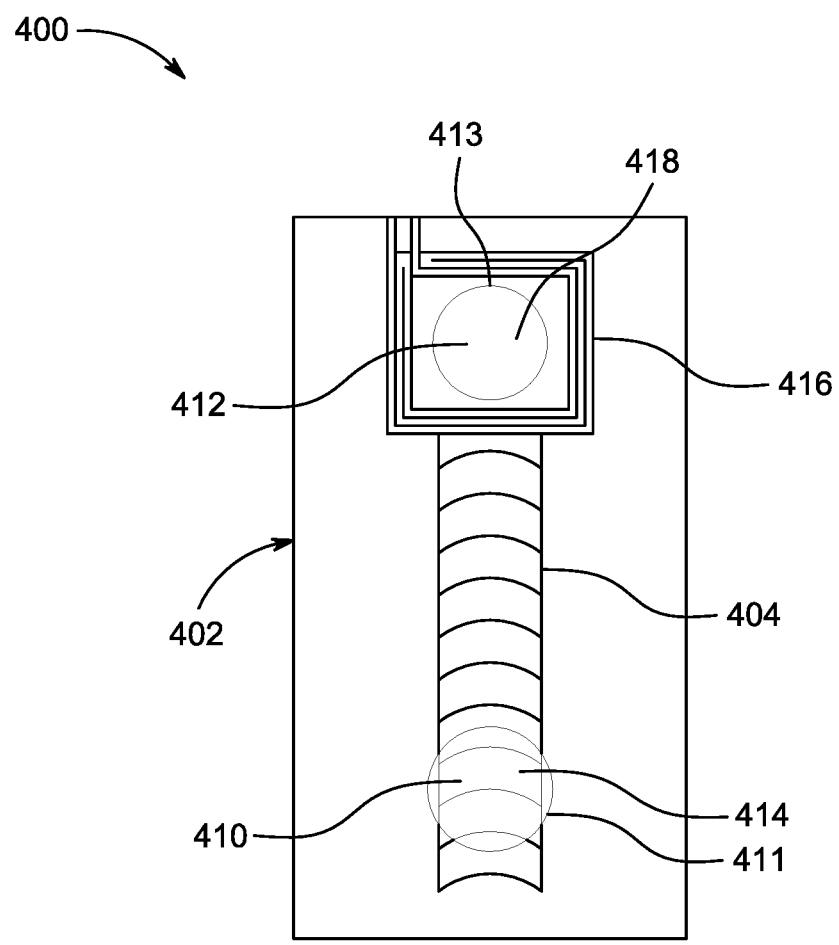
FIG. 4 is a top view of an ARC-based biomolecule processing device, according to another embodiment of the present arrangements.

While the embodiments of FIG. 3A-3C show a series of ARC tracks connected to and/or joined by various components, the present teachings recognize that other ARC-based device embodiments may provide for simpler configurations. To this end, FIG. 4 is a top view of an ARC-based biomolecule processing device 400, according to another embodiment of the present arrangements. A substrate 402, an ARC track 404, a transport solution receiving area 410, a transport solution droplet 411, a biomolecule sample receiving area 412, a biomolecule sample droplet 413, a microheater 416, and a heating area 418, are substantially similar to their counterparts in FIG. 3A, i.e., substrate 302, ARC track 304, transport solution receiving area 310, transport solution 311, microheater 316, and heating area 318. FIG. 4 also shows a biological sample receiving area 412 located at the same region as heating area 418. This provides the advantage of receiving a biomolecule sample droplet directly at heating area 418 (e.g. without requiring transport along an ARC track) for thermal processing (e.g., cellular lysis). Likewise, FIG. 4 shows reconstituting area 414 located at the same region as transport solution receiving area 410. This provides the similar advantage of reconstituting lyophilized reagents in a transport solution without requiring transport along an ARC track.

ARC-based biomolecule processing device 400 of FIG. 4 thus provides a system for carrying out biomolecule processing using a single ARC track connected to a microheater. The present teachings, however, contemplate use of many such single ARC-track/microheater configurations on a single substrate. Such single ARC track/microheater configurations may avoid the use of other ARC-based components, such as delivery junctions and/or ARC gates, providing for simpler and more manageable designs. In other embodiments of the present arrangements, however, a delivery junction and/or an ARC gate is used in the embodiment of FIG. 4.

Figure 5A:
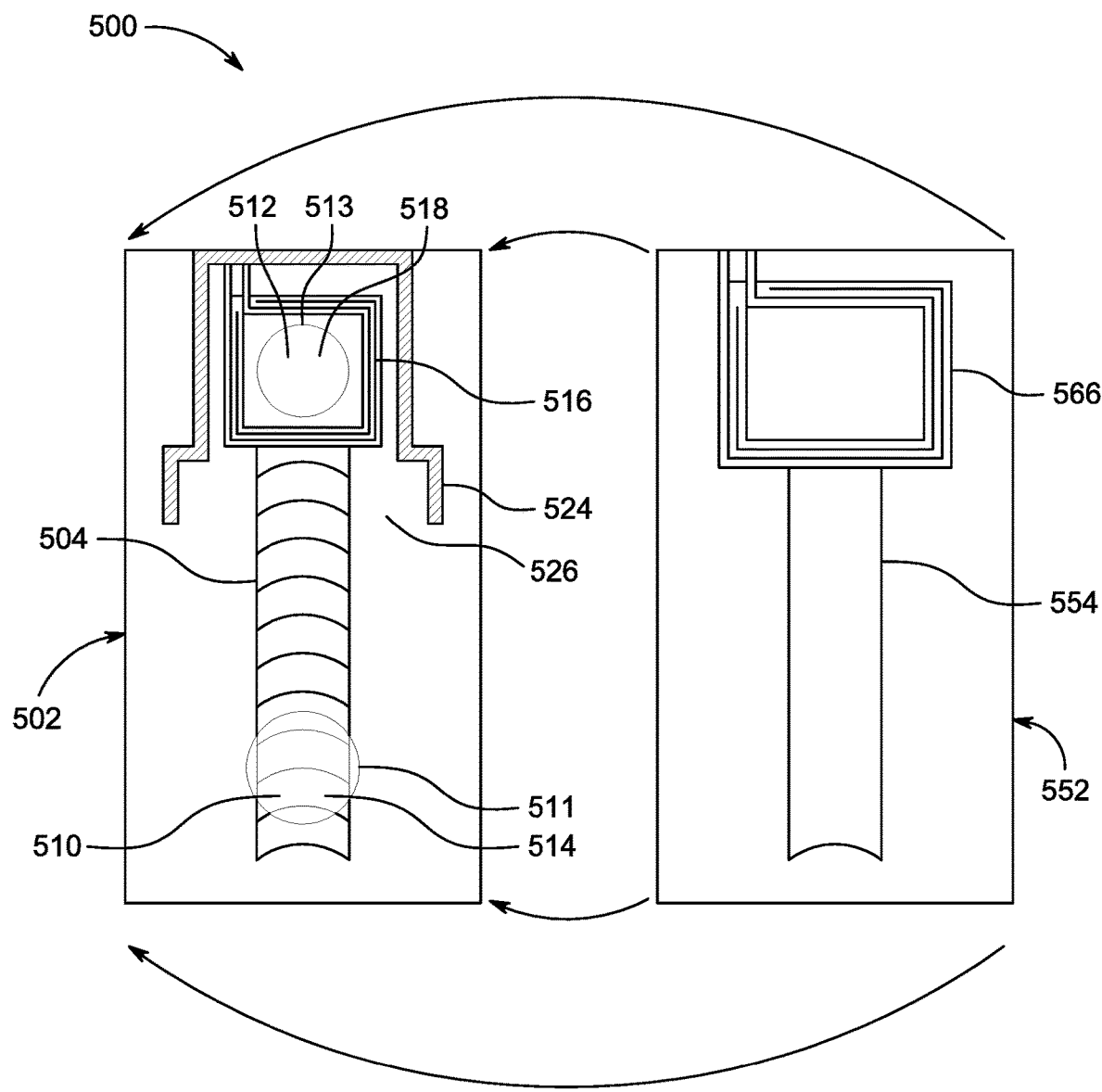
FIG. 5A is a top view of certain unassembled components used in a two-plated ARC-based biomolecule processing device, according to one embodiment of the present arrangements and with a transport solution droplet and a biomolecule sample droplet disposed thereon.
Figure 5B:
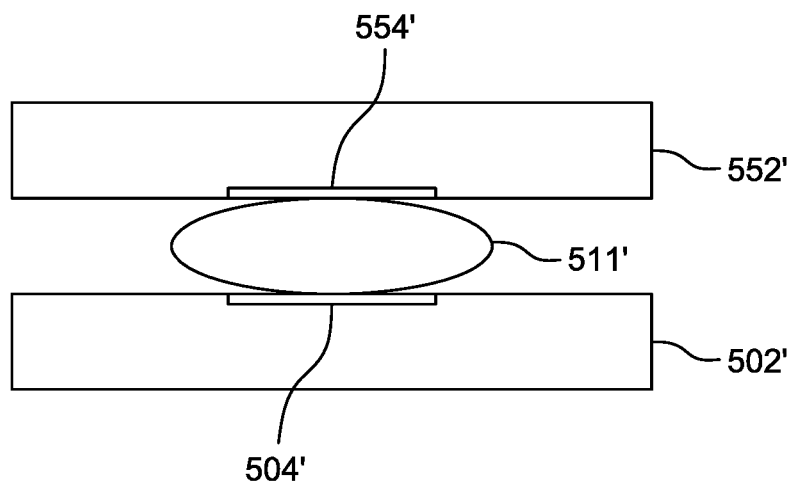
FIG. 5B is a side view of one end of the two-plated ARC-based biomolecule processing device of FIG. 5A in an assembled state.
Figure 5C:
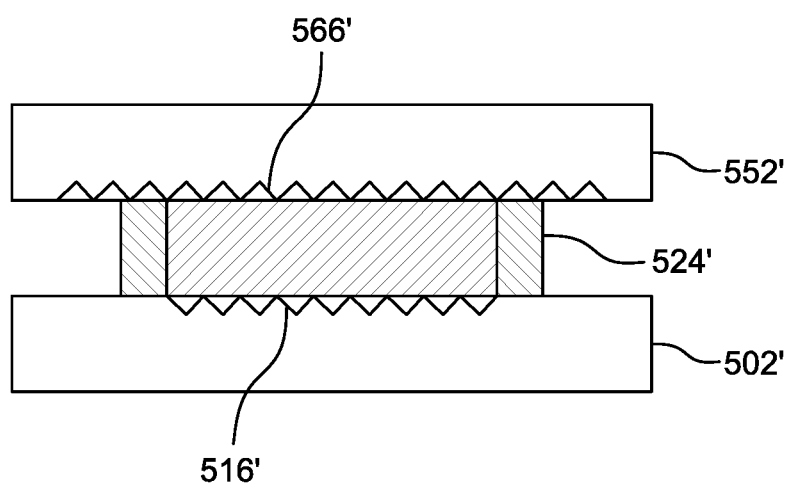
FIG. 5C is a side view of another end of the two-plated ARC-based biomolecule processing device of FIG. 5A in an assembled state.

The present teachings recognize that certain thermal processes carried out using one plate, or one substrate (e.g., as shown in FIGS. 3A-3C and 4), such one-plate configurations are open to surrounding air, and may be, under certain circumstances, susceptible to droplet evaporation and/or condensation heat processing steps. To address this, FIG. 5A shows certain components of a two-plated ARC-based biomolecule processing device 500, according to one embodiment of the present arrangements. Device 500 includes a bottom plate 502 having an ARC track 504, a transport solution receiving area 510, a biomolecule sample receiving area 512, a reconstituting area 514, a bottom microheater 516, a heating area 518, and a gasket 524; and a top plate 552 having a track 554 and a top microheater 566. FIG. 5A also shows a transport solution droplet 511 disposed on transport solution receiving area 510, which is in the same or similar location as reconstituting area 514, and a biomolecule sample droplet 513 disposed on biomolecule receiving area 512, which is in the same or similar location as heating area 518. While FIG. 5A shows plates 502 and 552 in an unassembled configuration, arrows in FIG. 5A show corners that are aligned when the plates are in an assembled configuration (i.e., as shown in FIGS. 5B and 5C, discussed below).

Bottom plate 502, ARC track 504, transport solution receiving area 510, transport solution droplet 511, biomolecule sample receiving area 512, biomolecule sample droplet 513, reconstituting area 514, and microheater 516, and heating area 518, are substantially similar to their counterparts described above with reference to FIG. 4, i.e., substrate 402, ARC track 404, transport solution receiving area 410, transport solution droplet 411, biomolecule sample receiving area 412, biomolecule sample 413, reconstituting area 414, microheater 416, and heating area 418. Bottom plate 502, however, also includes a gasket 524 with an aperture 526 defined therein. Aperture 526 provides an opening for transport of droplet 511 to microheater 516 when the present system is in use. In alternate embodiments of the present arrangements, gasket 524 partially or completely surrounds an outer edge of plate 502.

According to one preferred embodiment of the present arrangements, gasket 424 is comprised of a least one member selected from a group comprising polymethyldisiloxane, polyisoprene, polyurethane, butylrubber, polychloroprene, or polyvinylchloride.

Top plate 552 of system 500 includes a top track 554 and a top microheater 566. According to one embodiment of the present arrangements, top track 554 is an ARC track. According to another embodiment of the present arrangements top track 554 is a hydrophobic coating, preferably FOTS. While top microheater 566 is substantially similar to microheater 516 in many respects, it is configured to be wider and/or longer than bottom microheater 516.

FIG. 5B shows a side view of a bottom end of two-plated ARC-based biomolecule processing system 500 of FIG. 5A, according to one embodiment of the present arrangements, in an assembled state. The bottom end of the device may be thought of as the same end where transport solution 511 is shown in FIG. 5A. FIG. 5B includes a bottom plate 502', a top plate 552', a bottom ARC track 504', a top track 554', and a transport solution 511', which are substantially similar to their counterparts in FIG. 5A, bottom plate 502, top plate 552, bottom ARC track 504, top track 554, and transport solution 522.

FIG. 5C shows a side view of a top end of two-plated ARC-based biomolecule processing device 500 of FIG. 5A, according to one embodiment of the present arrangements, in an assembled state. A bottom plate 502', a bottom microheater 516', a gasket 524', a top plate 552' and a top microheater 566', are substantially similar to their counterparts in FIG. 5A, i.e., bottom plate 502, bottom microheater 516, gasket 524, top plate 552, and top microheater 566.

As shown in FIG. 5C, gasket 524' defines a distance, or a separation, between bottom plate 502' and top plate 552'. According to one embodiment of the present arrangements, gasket 552' defines a distance of between about 1 mm and about 3.5 mm, and preferably, between about 2 mm and about 2.5 mm, between bottom plate 552' and top plate 552".

Figure 6A:
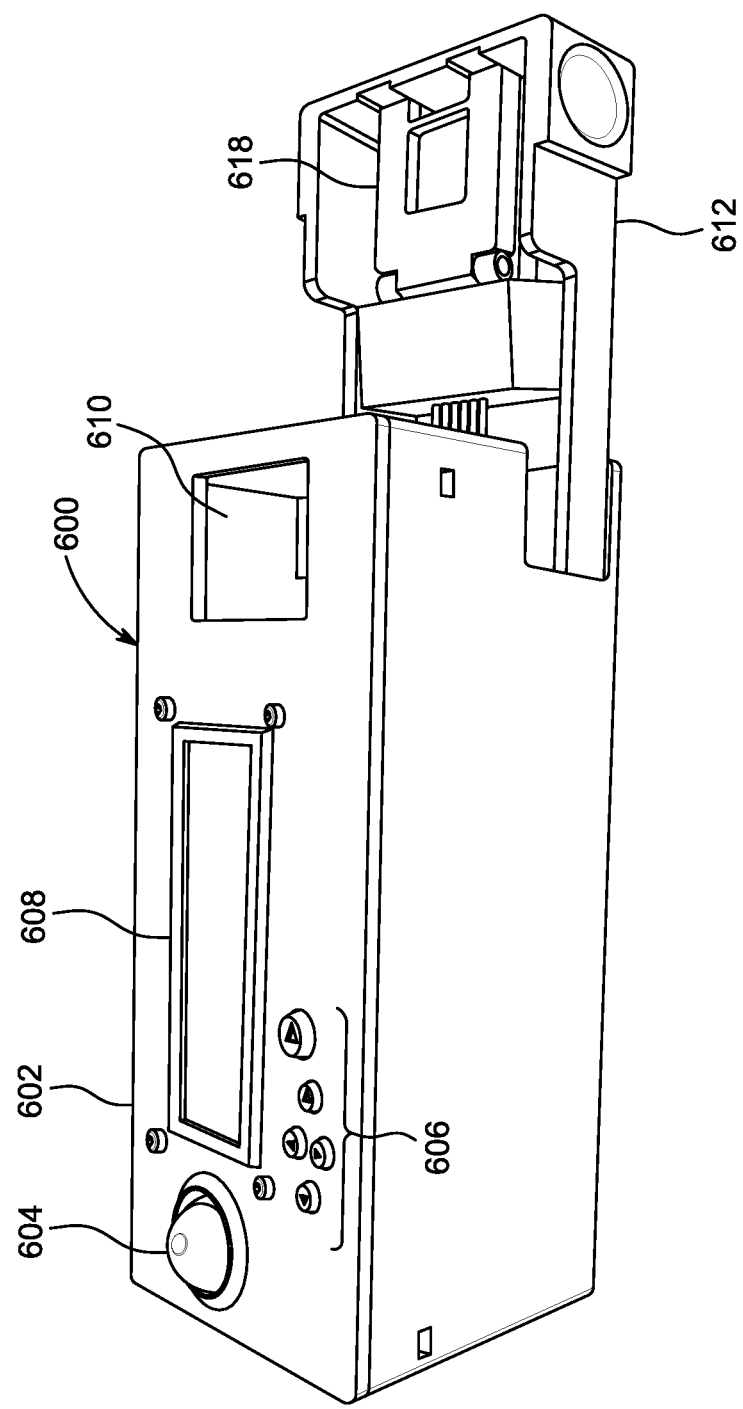
FIG. 6A is a perspective view of an exemplar portable driving unit, according to one embodiment of the present arrangements and in a retracted configuration with a cartridge containing an ARC-based biomolecule processing device secured therein.
Figure 6B:
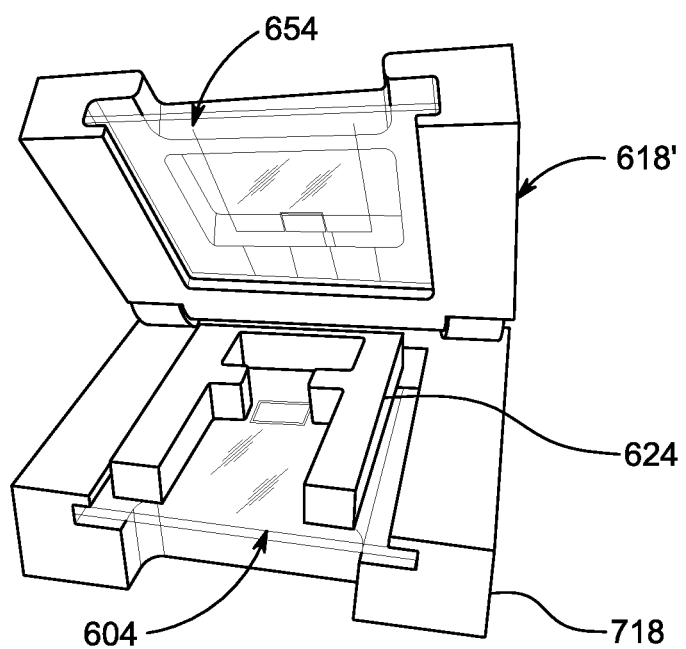
FIG. 6B is a front-perspective view of the cartridge in FIG. 6A in an open configuration.

The present teachings also contemplate other means of defining a distance between plates 502' and 552' when the present ARC designs are in an assembled state. By way of example, a cartridge may be fabricated to hold each of plates 502" and 552" (e.g., as shown in FIG. 6B) at an appropriate separation distance during use of the device.

The present teachings recognize that the two-plated configuration of FIGS. 5A-5C provides additional advantages of reducing droplet evaporation and/or condensation when the present systems are in use. In particular, certain design elements introduced into the two-plated system reduce both evaporation of droplets subjected to heat processing at a microheater and resulting condensation at other portions on the device. This is particularly advantageous in heat processing steps carried out at relatively high temperatures (e.g., lysis of biomolecule sample droplets at about 95° C.) and/or for an extended period of time (e.g., isothermal DNA amplification of DNA at about 65° C. for about 20 minutes).

As shown in FIG. 5A, gasket 524 is configured to surround microheater 518, providing an enclosure around the microheater that reduces surface area contacting fluid droplets during heating steps, thus reducing condensation and evaporation. Further, the use of a single-ARC track configuration of FIGS. 5A-5C minimizes open air space in the device, further slowing evaporation. Further still, top microheater 568 is configured to extend beyond the dimensions of bottom microheater 516, as shown in in FIG. 5C. Accordingly, while bottom microheater 516 carries out thermal heat processing of a fluid droplet, microheater 566 warms regions of bottom plate 502 that extend beyond the edges of microheater 518. Such warming of these regions on substrate 502, by top microheater 566, further prevents condensation and/ or evaporation without reaching temperatures high enough to risk damaging temperature sensitive reagents located on the substrate (e.g., at a reconstituting area). Use of a top microheater, while a bottom microheater carries out thermal processing, results in droplet volumes persisting for up to about 30 minutes when the two-plated arc-based devices of the present arrangements are in use, providing sufficient time to carry out many types of biomolecule processing protocols such as isothermal DNA amplification.

Further, those embodiments that employ a single ARC-track-configuration (including the two-plated configuration of FIGS. 5A-5C) provide certain efficiency advantages. By way of example, because a biomolecule sample droplet may be deposited directly on a heating area, and/or a transport solution may be deposited directly on a reconstituting area, use of this system requires only a single ARC track. By comparison, the embodiments of FIGS. 3A, 3B, and 3C, require advancement of a transfer solution along two ARC tracks and advancement of a biomolecule sample on a third ARC track. Similarly, providing a reconstituting area (e.g., reconstituting area 514) in the same location as transport solution receiving area (e.g., transport solution receiving area 510) also avoids the use of an ARC track that delivers transport solution to a reconstituting area (e.g., as shown in FIG. 2B).

The present teachings further recognize that droplet transport with use of the two-plated designs of the present arrangements is relatively independent of droplet volume within a range of droplet volumes that are neither too small to contact the top-plate, nor too large to sufficiently respond to the ARC track. Without wishing to be bound to theory, droplets within this range exhibit a similar ARC threshold profile. Because a wide range of droplet values may be used, this provides the advantage of a more user-friendly device, as it allows a large tolerance for application of droplets by a user who does not have access to precision-pipetting equipment or who lack the experience or skill to carry out pipetting in a precise and consistent manner.

While ARC-based biomolecule processing devices of the present arrangements provide novel and effective means of carrying out biomolecule processing (e.g., isothermal DNA amplification), further components may be coupled to these ARC-based devices to facilitate portability and in-field use, as well as ease of use by a non-technically trained end user. To this end, FIG. 6A shows a portable driving unit 600, according to one embodiment of the present arrangements. FIG. 6A includes a housing 602, a camera 604, a control panel 606, a viewing screen 608, a viewing area 612, a retractable cartridge platform 612, and a cartridge 618 secured in retractable cartridge platform 612.

Cartridge 618 may be thought of as a component that secures the ARC-based biomolecule processing devices of the present arrangements in portable driving unit 600 and couples the devices to other components (e.g., a power source). To this end, FIG. 6B shows a cartridge 618', which may be thought of as the same as cartridge 618 of FIG. 6A, but in an open configuration. As shown in FIG. 6B, cartridge 618' secures a bottom plate 602 and a top plate 652 with a gasket 624 disposed therebetween. Bottom plate 602, gasket 624, and top plate 652 are substantially similar to their counterparts in FIG. 5A, i.e., bottom plate 502, gasket 524, and top plate 552.

Cartridge 618 may be thought of as a device that secures the ARC-based processing devices of the present teachings in place and connects such device to other components in portable driving unit 600. Preferably, cartridge 614' is disposable and comprised of relatively inexpensive material, such as plastic or composites, rendering it appropriate for disposal (or recycling) after a single use. Retractable cartridge platform 612 in FIG. 6A is configured to secure cartridge 618 during ARC-based biomolecule processing according to the present teachings.

Other components shown in FIG. 6A may be used to facilitate in-field use of the present ARC-based processing devices. For example, control panel 606 and screen 608 will allow an end-user to carry out functions and protocols that have been programmed into software embedded in the portable driving unit. Likewise, camera 604 and viewing area 610 provide means for the end-user to observe and analyze processes carried out by ARC-based devices secured by cartridge 614.

In addition to the components on FIG. 6A, housing unit 600 may be configured with various other components located within housing unit 602. By way of example, housing unit 600 may include an electromagnetic motor, a solenoid, a generator, custom electric circuitry, a pre-amplifier, an amplifier, a battery, control hardware (e.g., a microcontroller or microprocessor board with embedded software), and on-board sensors (e.g., GPS, temperature, humidity, carbon dioxide, and pressure sensors) for environmental variables of concern to the sample test or use). Accordingly, portable driving unit 600 may provide an end-user a pre-programmed system that, by way of non-limiting examples, supplies energy for certain processing protocols (e.g., isothermal DNA amplification for purposes of species identification and/or validation); automates such processing protocols using pre-programmed software; captures and analyzes results of such processing protocols; provides the end-user control over the system by the use of a control panel and LCD screen; and provides desired inputs to the system (e.g., by use of sensors). Such components and features provide a non-technically trained end-user a system that requires little more than supplying fluid droplets on an ARC-based biomolecule processing device, placing the device in a cartridge, securing the cartridge in the portable driving unit, and initiating automated programs that carry out processing protocols. Further, the present teachings recognize that the portable driving unit of the present teachings and arrangements provide a modular platform that may be adapted for various other specific uses contemplated for the ARC-based devices of the present inventions.

Though not shown in FIG. 6A, portable driving unit 600 includes a vibration-driving sub-system that provides energy to generate orthogonal vibrations to ARC-based processing devices and to stimulate heat from microheaters. According to one preferred embodiment of the present arrangements, portable driving unit 600 uses a DC solenoid controlled with an Adriano Uno. To this end, FIG. 6C shows an exemplar circuit diagram 670 of an Arduino Uno coupled, via custom circuitry, to various components associated with portable driving unit 600, according to one embodiment of the present arrangements.

Figure 6C:
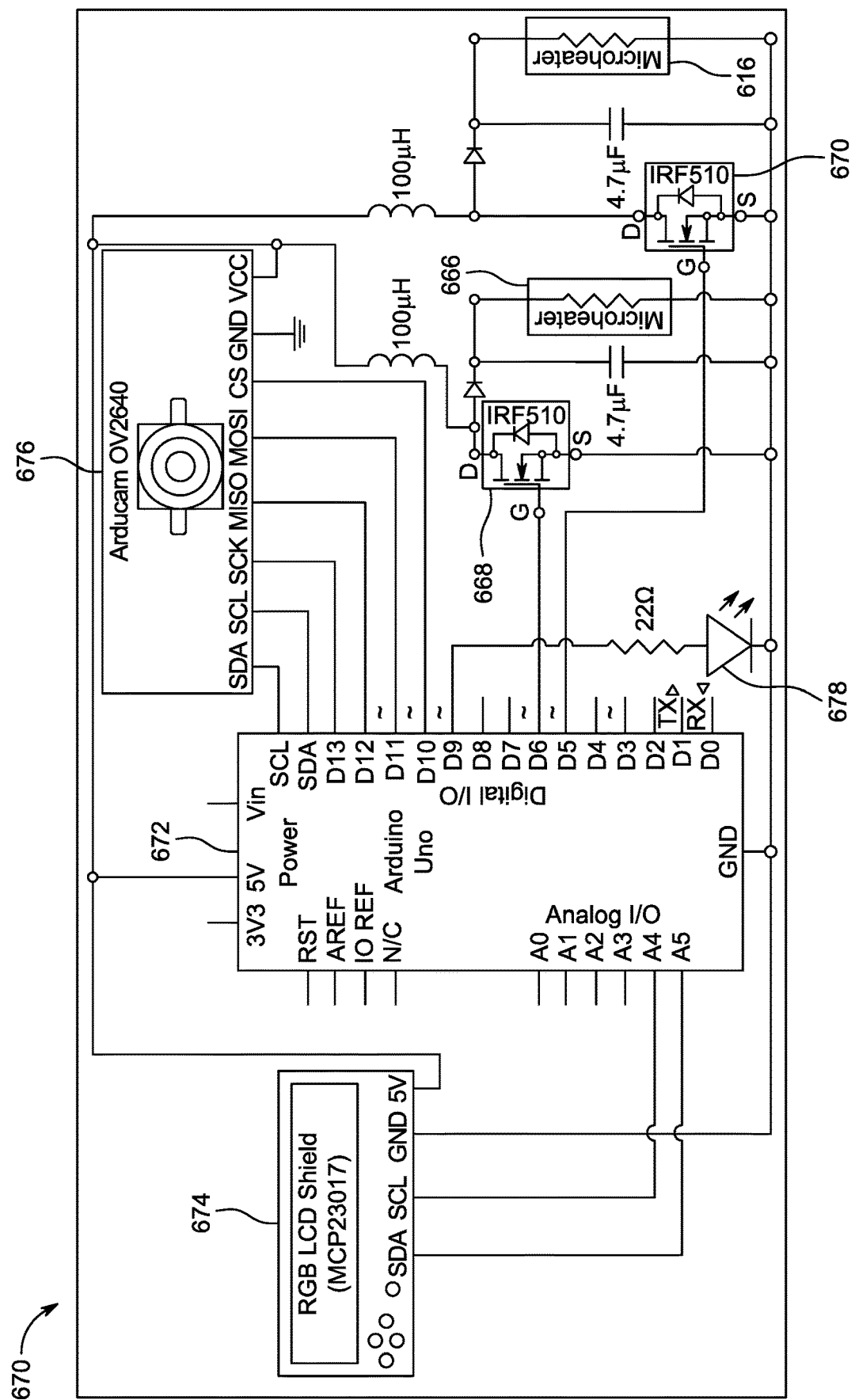
FIG. 6C is a circuit diagram showing certain electronic components coupled by custom circuitry, according to one embodiment of the present arrangements, to an ARC-based biomolecule processing device and a portable driving unit.

FIG. 6C shows Arduino Uno 672 coupled to a control panel and LCD screen 674 (e.g., an RGB LC Shield (MCP23017)), a camera 676 (e.g., an Arducam OV2640), a light-emitting diode 678, a microheater 618, a microheater 668, an N-channel metal-oxide-semiconductor field-effect transistor (MOFSET) 668, and a MOFSET 670. Preferably, MOFSET 668 and/or MOFSET 670 is used as a precision switch to connect the power supply directly to the solenoid. The signal from the Arduino is thus applied to the gate of the MOSFET, metering power to the solenoid in pulses of the desired frequency necessary to provide vibrational energy.

Figure 7:
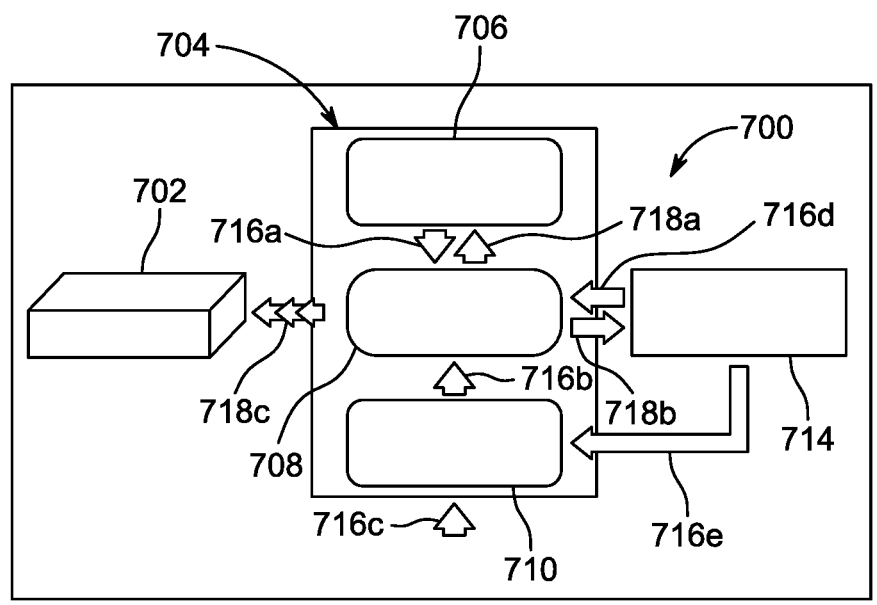
FIG. 7 is a system flow diagram showing delivery of information between certain components of an ARC-based biomolecule processing system, according to one embodiment of the present arrangements.

FIG. 7 is a system flow diagram showing certain components of a system 700 for carrying out ARC-mediated biomolecule processing, according to one embodiment of the present arrangements. System 700 includes a database 702, a portable driving unit 704, and a cartridge 708. Portable driving unit 704 and cartridge 708 are substantially similar to their counterparts described above with reference to FIGS. 6A and 6B. Portable driving unit 704 includes a user interface 706, controlling hardware 708, and sensors/detectors 710. Arrows 716a, 716b, and 716c show flow of information into portable driving unit 704. Arrows 718a, 718b, and 718c show flow of information between the components located in portable driving unit 704. Arrow 720 shows flow of information from portable driving unit 706 to cartridge 714. Arrows 722 show flow of information from portable driving unit 204 to database 702.

Database 702 is any database well-known to those of skill in the art. By way of example, database 202 is capable of incorporating information received from sensors/detectors 710 and user input from user interface 706 to create an extensive database incorporating and organizing metadata from on-board sensors and user input with tests results.

Conventional, in-laboratory DNA amplification techniques typically accomplish species identification by processing and amplifying a sample in the laboratory with traditional polymerase chain reaction (PCR) techniques, which employ a thermocycling process that requires cyclical changes in process temperatures, generally repeated up to 30 times. The amplicons produced from PCR techniques are then sequenced or measured for fragment length. The sequencing reads or fragment analyses are then compared to reference samples to provide a definitive species identification. While the present systems and methods may be configured and adapted to carry out PCR DNA amplification, other DNA amplification techniques are better suited to the in-field objectives of the present arrangements and teachings.

According to preferred embodiments of the present arrangements, loop-based isothermal amplification, or LAMP, is carried out on the ARC-based processing devices of the present teachings to facilitate species identification and/or validation. The present teaching recognize that LAMP has one of the fastest reaction times of isothermal amplification techniques, producing detectable product in as little as 15 minutes. Further, LAMP does not require additional enzymes or proteins for molecular probes to reach their target or require a single stranded target. Further still, LAMP produces copies of the target and regions between the target sequences.

LAMP amplification is achieved through the use of four to six primers and typically uses a version a *Bacillus stearothermophilus* (Bst) polymerase, or similar polymerase with strand displacement that has an optimal efficiency between about 60° C. and about 65° C. Further, by use of specific primers, LAMP does not require any sequencing.

The present teachings further recognize that LAMP primers used to initiate DNA amplification may be based on certain "DNA barcodes" known and publicly available for various species. A DNA barcode may be thought of as a genetic sequence that is unique to species, but varies little, or is conserved, between individuals within a species. DNA barcodes depend on a divergence gap, or a separation between intra- and inter-species variation within the target sequence. In other words, DNA barcodes are thought to be conserved within species but vary between species, making them appropriate for use in species identification and/or validation. By way of non-limiting example, the mitochondrial cytochrome oxygenase gene (COI) is known to be very conserved among certain *O. tshawytscha* salmon species. On the other hand, the COI gene is divergent among different salmon species (e.g., *Oncorhynchus nerka, Oncorhynchus kisutch,* or *Salmo salar*). LAMP primers based on the COI gene may thus be used to produce DNA amplicons during LAMP that are used to validate the presence of the *O. tshawytscha* salmon species and/or to distinguish *O. tshawytscha* from other salmon species, such as *Oncorhynchus nerka, Oncorhynchus kisutch,* or *Salmo salar*. In such manner, amplification of DNA barcode regions (e.g., by LAMP) may be used to identify or otherwise validate presence of a species (e.g., in food).

FIG. 8 shows certain salient steps of process 800 for carrying out biomolecule processing according to one embodiment of the present teachings. As set forth in various examples below associated with various process steps, process 800 is particularly appropriate to for carrying out LAMP using the ARC-based processing devices of the present teachings and arrangements.

Process 800 begins with a step 802, which includes receiving a biomolecule at or near a biomolecule receiving area (e.g. biomolecule receiving area 512 of FIG. 5A). Preferably, the biomolecule receiving area is the same as a heating area (e.g. heating area 518 of FIG. 5A) and has a microheater disposed on or around the heating area.

Biomolecule is preferably a sample containing DNA of a species desired to be identified or otherwise validated. The sample is contained or suspended in a fluid (e.g., water or buffer). Preferably, the fluid has a volume that is between about 5 μL and about 20 μL.

The species may be of plant, animal, or marine origin. In other embodiments of the present teachings, however, a biomolecule sample is or includes RNA or protein. In yet other embodiments of the present teachings, a biomolecule is not used; rather, inorganic material to be tested or characterized is used.

In preferred embodiments of the present teachings, certain reagents or components have been lyophilized on the heating area. By way of example, non-temperature-sensitive reagents or components necessary to isothermal DNA amplification (e.g., LAMP) may be lyophilized or dried on the heating area or the microheater prior to use of the device. Such lyophilized or dried materials will also be resuspended and/or dissolved in fluid containing biomolecule.

Next, a step 804 includes receiving a transport solution at or near a transport solution receiving area (e.g. transport solution receiving area 510 of FIG. 5A). Preferably, transport solution receiving area is also a reconstituting area (e.g., reconstituting area 514 of FIG. 5A) that contains lyophilized or dried reagents or materials that were placed there prior to use of the present device. Such reagents or materials may include temperature-sensitive materials that will remain in place until the biomolecule sample is subjected to heat processing. According to one embodiment of the present arrangements, such temperature-sensitive lyophilized or dried reagents include a *Bacillus stearothermophilus* (Bst) polymerase used in LAMP.

Once dissolved or suspended in transport solution, a reconstituted reagent solution or suspension is produced. Preferably, the reconstituting area is located on an ARC track (e.g., ARC track 504 of FIG. 5A) connected to downstream microheater (e.g., microheater 516 of FIG. 5A).

Next, a step 806 includes heating the biomolecule fluid sample at the heating area (e.g., heating area 518 of FIG. 5A) to produce an intermediate biomolecule. Preferably, the biomolecule fluid sample is processed at conditions sufficient to cause lysis. By way of example, the sample is heated for about 20 minutes at about 65° C. to lyse the cells and expose DNA for downstream isothermal amplification.

Next, in those embodiments where a reconstituting area is not also a transport solution area, a step 810 includes reconstituting dry reagents into transport solution at the reconstituting area to produce a reconstituted reagent solution. Such reconstituting of reagents (e.g., those for use in LAMP) may be facilitated by supplied vibrational energy.

Next, a step 12 includes conveying, using a vibration-driving subsystem and an ARC track (e.g. ARC track 504 of FIG. 5A), the reconstituted reagent solution or suspension from the ARC track to the heating area. According to one embodiment of the present teachings, conveying on the ARC track is carried out by delivering vibrations at a frequency that is less than about 60 Hz and a vibration amplitude that is between about 2.0 g and about 4.0 g, and preferably, about 3.0 g. In another embodiment of the present teachings, delivering vibrations produces a substrate displacement that is greater than about 300 μm.

In certain embodiments of the present teachings, the substrate containing the ARC track is tilted towards the heating area to facilitate conveyance of the reconstituted reagent solution or suspension to the heating area. Such tilting may be used to help overcome an ARC threshold. Preferably, such tilting produces an angle between the substrate and a flat, horizontal surface that is between about 5° and about 15°. The present teachings further recognize that tilting may be useful to initiate and/or facilitate transport of fluid droplets on ARC tracks where, due to the presence of certain reagents or components, the fluid droplets have a reduced surface tension.

In certain embodiments of the present teachings, conveyance of reconstituted reagent solution and/or suspension to a heating area will require passage through an aperture defined by a gasket (e.g., aperture 526 of gasket 524 of FIG. 5A).

Next, a step 814 includes processing the reconstituted reagent solution in the presence of the intermediate biomolecule, at the heating area, to produce a processed biomolecule. In preferred embodiments of the present teachings, processing in step 814 includes isothermal DNA amplification (e.g., LAMP). In such embodiments, processing may be carried out for between about 15 minute and about 25 minutes at about 60° C. to about 75° C., or preferably, for about 20 minutes at about 65° C. to accomplish isothermal DNA amplification.

The present teachings recognize that this is an extremely energy efficient process. Generally, a 5-minute lysis step (e.g., step 806) at about 95° C. and the 20-minute amplification step (e.g., step 814) at about 65° C. consumes about 0.30 Wh.

DNA amplicons produced during LAMP DNA amplification according to the present teachings (e.g., process 800) may be used to facilitate species identification. In particular, isothermal DNA amplification techniques such as LAMP are particularly useful, as the target sequences (or in some cases the molecular probes), are continuously being replicated throughout the entire reaction process. Thus, unlike PCR, which produces many identical amplicons, isothermal amplification reactions result in a relatively larger DNA product.

Furthermore, because LAMP is continuous and not staged in cycles, the formation of a detectable DNA product occurs much more rapidly compared to traditional thermocyclic PCR. The present teachings recognize that these large DNA products formed during isothermal amplification often allow for detection methods that target the byproducts of the reaction, such as hydrogen (pH) or pyrophosphate. These alternative detection approaches, which can be performed with minimal equipment or with the naked eye, make isothermal amplification methods very effective for use in low-resource settings. Moreover, the simplicity of a single temperature step, rather than requiring a control system to enable thermocycling, makes isothermal amplification appropriate for the systems and methods of the present inventions.

Further, in the field, definitive species identification is rarely necessary. Rather, end-users are often more interested in validating the presence of a target species or distinguishing a species from a small number of alternatives. By way of example, in seafood inspection, the user must confirm that the product is consistent with its label rather than determining exactly what species the product is.

Similarly, in invasive species monitoring, a user is more interested in determining if the target species was present or not, rather than profiling the entire biodiversity of the sample. Therefore, a qualitative result for target species is sufficient for this application.

Accordingly, the systems and methods of the present invention are particularly well-suited to isothermal DNA amplification techniques that are carried out on the ARC devices and processes disclosed herein.

EXAMPLES

Example 1

Fabrication of ARC Tracks on Substrate

Fabrication of silicon dioxide ($SiO_2$) ARCs begins by cleaning the wafer with oxygen plasma (Glow Research). This removes any dust or organic contaminates and ensures hydroxyl groups are present at the surface. The wafer is then coated with a negative resist, with a thickness of approximately 1.1 µm. The negative resist (NR9-1000PY) is exposed (about 315-400 nm) with a contact aligner (ABM) or mask writer (Heidelberg) prior to development in a solution of approximately 3:1 AD10 to deionized water. Proceeding to development, substrates are cleaned briefly with oxygen plasma to remove any residual undeveloped photoresist, but not long enough to affect the developed pattern. A coating of hydrophobic silane (fluorooctyltrichlorosilane (FOTS)) is applied to the wafers via vapor deposition. Stripping the resist reveals a transparent pattern of $SiO_2$ ARCs defined by the hydrophobic FOTS background. Finally, the wafer is baked on a hot plate (at about 150° C. for about 15 minutes) to anneal the FOTS, creating covalent siloxane bonds, to improve long-term stability.

Example 2

Fabrication of Substrate

Isothermal chips are fabricated from glass wafers to provide a transparent viewing window and reduced thermal conductivity compared to silicon. Soda-lime glass wafers are first coated with approximately 350 nm of Molybdenum through an evaporation process. The Molybdenum is patterned with a positive (AZ1512) photoresist, and developed with a solution of 1:4 AZ340 to deionized water. Exposed molybdenum is removed by a highly anisotropic etch back process using an inductively couple plasma tool with fluorine gases (Oxford). Remaining photoresist is stripped using wet chemistry (EKC) as removal with oxygen creates adhesion issues to molybdenum in subsequent steps. The thickness of the Molybdenum thin-film is confirmed at this step using a profilometer (Tecron Alphastep-200). The wafer is then capped with a 1 µm layer of silicon dioxide using a plasma enhanced chemical vapor deposition process (PECVD). Contact pads are released by patterning the oxide cap with photoresist and etching the exposed oxide above the contact pads with buffered oxide etchant (BOE) for 6 min. The wafers are then diced into 2 cm×2.5 cm chips with a 150 µm thick diamond saw blade (Disco).

Example 3

Characterization of Microheater Dimensions

Microheaters used in Example 3 are composed of molybdenum with a thickness of approximately 350 nm. Multiple designs of the microheater were examined. In this case, a balance between power consumption and voltage must be carefully considered. Reducing the amount of material reduces power consumption, but also increases the resistance of the microheater. When resistance is increased, a higher voltage is required to conduct sufficient current through the device to hit target temperatures. At a certain point, the required voltage will be too high for a portable device to be practical.

Figure 9A:
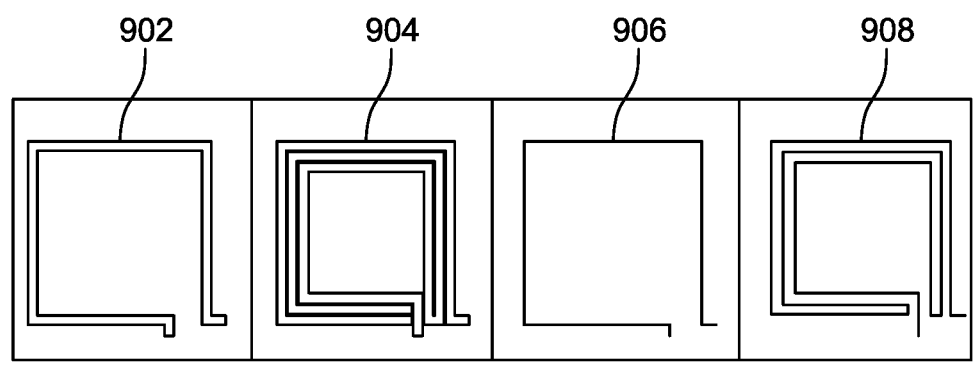
FIG. 9A shows four exemplar microheaters, according to alternate embodiments of the present arrangements, constructed from leads of varying lengths and widths.
Figures 9B, 9C:
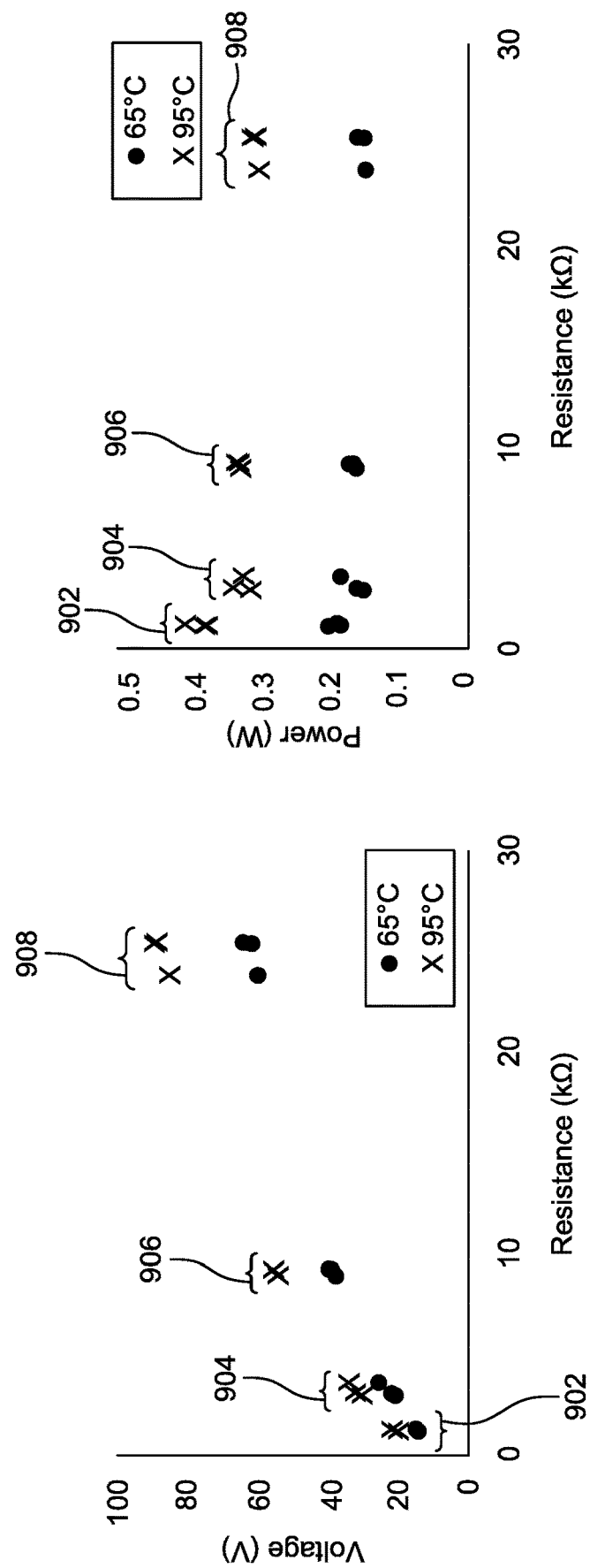
FIG. 9B shows a graph depicting a relationship between voltage and resistance when the exemplar microheaters of FIG. 10A are used to process samples at about 65° C. and at about 95° C.
FIG. 9C shows a graph depicting the relationship between power and resistance when the exemplar microheaters of FIG. 10A are used to process samples at about 65° C. and at about 95° C.

As shown in FIG. 3A, designs tested for voltage and power in FIGS. 9B and 9C consisted of thick (~250 µm width) and thin (~25 µm width) leads that formed the microheater through a single (short) or triple (long) winding. Accordingly, microheater 902 is a short and thick microheater, microheater 904 is a long and thick microheater, microheater 906 is a short and thin microheater, and microheater 1008 is a long and thin microheater.

As shown in FIG. 9B, microheater 904 exhibited the lowest resistance and required the lowest voltage to hit the temperature targets. Conversely, microheater 908 exhibited the highest resistance and required the highest voltage to hit the target temperature. If the microheater was the only component of this system, it would be expected that microheater 906 would be the most power efficient, as it would have the smallest amount of the resistive heating material that is required to be heated. Consequently, microheater 904, with the largest mass of molybdenum, would be expected to be the least efficient.

However, in this case the microheater must also heat up the entire region of glass about which the droplet will be present. The mass of this glass will remain constant, regardless of the microheater design, and the glass will also be cooling to the outside environment.

As such, as shown in FIG. 9C, both thin microheaters 902 and 906 and thick microheater 904 all exhibit similar power efficiencies for heating the system to the lysis temperature of about 95° C. and the LAMP reaction temperature of about 65° C. However, microheater 902 had a slightly higher power consumption than the other three, particularly at the higher 95° C. temperature target. Thus, the heater that was expected to be the least efficient exhibited the same efficiency as the heater expected to be the most efficient. This effect is likely due to the surface area of the heater offsetting the cooling rate of the glass substrate.

The present teachings recognize, then, that microheater 904 is well-suited to the designs of the present ARC-based processing devices. Nevertheless, microheaters 902, 906, and 908 may also be appropriate for use on such devices.

Although illustrative embodiments of the present arrangements and teachings have been shown and described, other modifications, changes, and substitutions are intended. Accordingly, it is appropriate that the appended claims be construed broadly and in a manner consistent with the scope of the disclosure, as set forth in the following claims.

What is claimed is:

1. A biomolecule processing device comprising:
   a substrate;
   a first anisotropic ratchet conveyor ("ARC") track defined on or within said substrate and having disposed at or near one end a biomolecule receiving area, which is configured to receive biomolecules;
   a microheater area disposed at or near another end of said first ARC track, microfabricated with a microheater, which is configured to heat the biomolecules that are received through said first ARC track from said biomolecule receiving area;
   a second ARC track defined on or within said substrate and having disposed at or near one end a transport solution receiving area and having disposed at or near another end a reconstituting area, wherein said transport solution receiving area is configured to receive transport solution, wherein said reconstituting area is configured to receive dry reagents and configured to reconstitute said dry reagents into reagent solution and/or suspension;
   a third ARC track defined on or within said substrate and that intersects with said first ARC track and said first microheater on said second ARC track such that said third ARC track is configured to convey reconstituted reagent solution and/or suspension to said microheater area for processing; and
   wherein each of said first ARC track, said second ARC track, and said third ARC track includes an arrangement of a plurality of hydrophilic rungs disposed on a hydrophobic region such that between two consecutive said hydrophobic rungs, a portion of said hydrophobic region is exposed.

2. The biomolecule processing device of claim 1, wherein said first ARC track and said second ARC track extend parallel to each other.

3. The biomolecule processing device of claim 1, wherein said third ARC track extends perpendicular to said first ARC track and said second ARC track.

4. The biomolecule processing device of claim 3, further comprising a delivery junction that is disposed between said second ARC track and said third ARC track such that said delivery junction facilitates transport of said reconstituted reagent solution and/or suspension from said second ARC track to said microheater, and wherein said delivery junction includes one or more substantially linear hydrophilic guides that extend from said hydrophilic rungs of said second ARC track to said third ARC track, wherein said hydrophilic rung is convex-shaped with a protruding portion extending in a direction towards said third ARC track and said substantially linear hydrophilic guides extend in said direction towards said third ARC track, and wherein said substantially linear hydrophilic guides are perpendicular to a plane or a line that tangentially intersects said protruding portion of said hydrophilic rung.

5. The biomolecule processing device of claim 1, wherein said dry reagents include at least one member selected from a group comprising, ionic salt, polymerase, primer, and surfactant.

6. The biomolecule processing device of claim 1, wherein said heating area and/or said microheater are designed to receive dried reagents and/or surfactant.

7. The biomolecule processing device of claim 1, wherein said one or more rungs is comprised of $SiO_2$.

8. The biomolecule processing device of claim 1, wherein said microheater is comprised of molybdenum.

9. The biomolecule processing device of claim 1, wherein said substrate is a soda-lime glass wafer.

10. A biomolecule processing device comprising:
    a first substrate, comprising:
    an anisotropic ratchet conveyor ("ARC") track defined on or within said first substrate and including a biomolecule receiving area, which is configured to receive biomolecules, and a reconstituting area, which is configured to contain dry reagents and is configured to receive a transport solution such that at said reconstituting area, dry reagents are reconstituted with the transport solution;
    a first microheater area disposed at or near said biomolecule receiving area, fitted with a first microheater, which is configured to heat the biomolecules that are received through said biomolecule receiving area and configured to process the heated biomolecules and the dry reagents reconstituted with the transport solution; and
    wherein said ARC track includes an arrangement of a plurality of hydrophilic rungs disposed on a hydrophobic region such that between two consecutive said hydrophobic rungs, a portion of said hydrophobic region is exposed.

11. The biomolecule processing device of claim 10, further comprising:
    a gasket that does not completely surround said first microheater and that provides an aperture that is defined to receive said reagent solution and/or suspension;
    a second substrate, comprising:
        a track defined on or within said second substrate; and
        a second microheater area disposed at or near an end of said track, microfabricated with a second microheater; and
    wherein in an assembled state of said first substrate and said second substrate, said first substrate is disposed underneath or adjacent to said second substrate such that said ARC track is opposite to and facing said track, said first microheater is opposite to and facing said second microheater, and wherein said second microheater occupies a greater surface area than said first microheater.

12. The biomolecule processing device of claim 11, wherein a distance between said first substrate and said second substrate is defined by said gasket.

13. The biomolecule processing device of claim 11, wherein said track is an ARC track and/or is a hydrophobic coating.

14. The biomolecule processing device of claim 10, wherein said dry reagents include at least one member selected from a group comprising primer, ionic salt, and polymerase.

15. The biomolecule processing device of claim 14, wherein said dry reagents are temperature-sensitive at temperatures that are greater than at least about 65° C.

16. A biomolecule processing system comprising:
    a vibration-driving subsystem; and
    a biomolecule processing device coupled to said vibration-driving subsystem, said biomolecule processing device comprising:
    a substrate;
    an anisotropic ratchet conveyor ("ARC") track defined on or within said substrate and including a biomolecule receiving area, which is designed to receive biomolecule, and a reconstituting area, which is designed to contain dry reagents and is designed to receive a transport solution such that at said reconstituting area, dry reagents are reconstituted with transport solution; and a microheater area disposed at or near said biomolecule receiving area, fitted with a microheater, which is designed to heat biomolecule that is received through said biomolecule receiving area and designed to process heated biomolecule and dry reagents reconstituted with transport solution;

and wherein said vibration-driving subsystem is configured to deliver orthogonal vibration waves to said substrate.

17. A method for processing biomolecules comprising:
receiving biomolecules at or near a biomolecule receiving area;
receiving a transport solution at or near a transport solution receiving area;
conveying, using a vibration-driving subsystem that delivers orthogonal vibration signals, said biomolecules along a first anisotropic ratchet conveyor ("ARC") track to a heating area, and said transport solution along a second ARC track to a reconstituting area;
heating, at said heating area, said biomolecules to produce intermediate biomolecules; reconstituting, at reconstituting area, said transport solution in the presence of one or more dry reagents to produce a reconstituted reagent solution and/or suspension;
delivering, using a delivery junction and said vibration-driving subsystem that delivers said orthogonal vibration signals, said reconstituted reagent solution and/or suspension from said second ARC track to a third ARC track; and
advancing, using said vibration-driving subsystem that delivers said orthogonal vibration signals, said reconstituted reagent solution and/or suspension from said third ARC track to said heating area; and
processing, at said heating area, said reconstituted reagent solution and/or suspension in the presence of the intermediate biomolecules to produce a processed biomolecules.

18. The method for processing biomolecules of claim 17, wherein during said conveying, said vibration-driving subsystem delivers said orthogonal vibration signals at a first frequency, during said delivering, said vibration-driving subsystem delivers said orthogonal vibration signals at a second frequency, and during said advancing, said vibration-driving subsystem delivers said orthogonal vibration signals at said first frequency.

19. The method for processing biomolecules of claim 17, wherein said delivery junction is configured to pause said reconstituted reagent and/or suspension during said conveying.

20. The method for processing biomolecules of claim 17, wherein said conveying, said delivering, and/or said advancing is carried out on a tilted substrate that is disposed at an angle, relative to a flat and horizontal surface, of between about 50 and about 15°.

21. A method for processing biomolecules comprising:
receiving said biomolecules at or near a biomolecule receiving area, wherein said biomolecule receiving area is located at or on a heating area;
receiving a transport solution at or near a transport solution receiving area, wherein said transport solution receiving area is also a reconstituting area;
heating, at said heating area, said biomolecules to produce intermediate biomolecules; reconstituting, at reconstituting area, said transport solution in the presence of one or more dry reagents to produce a reconstituted reagent solution and/or suspension;
conveying, using a vibration-driving subsystem and an anisotropic ratchet conveyor ("ARC") track, said reconstituted reagent solution and/or suspension from said ARC track to said heating area; and
processing, at said heating area, said reconstituted reagent solution and/or suspension in the presence of the intermediate biomolecules to produce processed biomolecules.

22. The method for processing biomolecules of claim 20, wherein said heating is carried out at a temperature that is about 95° C. and said intermediate biomolecules are lysed.

23. The method for processing biomolecules of claim 21, wherein said processing includes carrying out isothermal DNA amplification at a temperature that is about 65° C. to produce a sample containing amplified DNA product.

24. The method for processing biomolecules of claim 22, wherein said processing includes carrying out loop-mediated isothermal DNA amplification to produce a sample containing amplified DNA product.

25. The method for processing biomolecules of claim 23, wherein said sample containing amplified DNA product is analyzed to confirm the identity of a plant or animal species from which said biomolecules were obtained.

26. A process for species identification comprising:
receiving, on an anisotropic ratchet conveyor ("ARC") track defined on a substrate, a sample containing DNA;
lysing said sample containing DNA at or on a microheater at a temperature that is between about 90° C. and about 100° C. to produce a lysed sample;
reducing said temperature to a temperature that is between about 60° C. and about 75° C.;
delivering, on said ARC track, a buffer with reagents for isothermal DNA amplification to said microheater to mix with said lysed sample to produce a sample and reagent mixture;
heating said sample and reagent mixture at between about 60° C. and about 75° C. for between about 15 minutes and about 25 minutes to produce a sample containing amplified DNA; and
analyzing said sample containing amplified DNA to carry out said species identification.

27. The process for species identification of claim 26, wherein at least some of said reagents for isothermal DNA amplification are lyophilized on said microheater and reconstituted in said lysed sample during said lysing.

28. The process for species identification of claim 25, wherein said analyzing said amplified DNA to carry out species identification includes at least one member selected from a group comprising: validating presence of species source of said sample containing DNA, determining species source of said sample containing DNA, and distinguishing species source of said sample containing DNA from known alternatives.

29. The process for species identification of claim 25, wherein said receiving is carried out on said microheater.

30. The process for species identification of claim 25, wherein following said receiving, said sample containing DNA is delivered to said microheater using said ARC track.

31. The process for species identification of claim 25, wherein said heating said processed sample includes performing loop-mediated DNA amplification.

* * * * *